(12) United States Patent
Beyenal et al.

(10) Patent No.: US 11,229,714 B2
(45) Date of Patent: Jan. 25, 2022

(54) ELECTROCHEMICAL REDUCTION OR PREVENTION OF INFECTIONS

(71) Applicant: WASHINGTON STATE UNIVERSITY, Pullman, WA (US)

(72) Inventors: Haluk Beyenal, Pullman, WA (US); Douglas Ruben Call, Pullman, WA (US); Boel Anita Fransson, Pullman, WA (US); Sujala Tajneen Sultana, Pullman, WA (US)

(73) Assignee: Washington State University, Pullman, WA (US)

( * ) Notice: Subject to any disclaimer, the term of this patent is extended or adjusted under 35 U.S.C. 154(b) by 776 days.

(21) Appl. No.: 15/743,605

(22) PCT Filed: Jul. 14, 2016

(86) PCT No.: PCT/US2016/042225
§ 371 (c)(1),
(2) Date: Jan. 10, 2018

(87) PCT Pub. No.: WO2017/011635
PCT Pub. Date: Jan. 19, 2017

(65) Prior Publication Data
US 2018/0207301 A1 Jul. 26, 2018

Related U.S. Application Data

(60) Provisional application No. 62/192,164, filed on Jul. 14, 2015, provisional application No. 62/311,747, filed on Mar. 22, 2016.

(51) Int. Cl.
*A61L 2/03* (2006.01)
*A61F 13/00* (2006.01)
(Continued)

(52) U.S. Cl.
CPC ............ *A61L 2/03* (2013.01); *A61L 2/186* (2013.01); *A61N 1/0428* (2013.01);
(Continued)

(58) Field of Classification Search
CPC .. A61L 2/186; A61L 2/03; A61N 1/20; A61N 2/30; A61N 2/205; A61N 1/0468;
(Continued)

(56) References Cited

U.S. PATENT DOCUMENTS

2003/0097090 A1 5/2003 Mori et al.
2003/0097845 A1* 5/2003 Saunders ............... A61F 7/007
62/3.3
(Continued)

FOREIGN PATENT DOCUMENTS

EP 1693073 A2 8/2006
WO WO9632082 A1 10/1996
(Continued)

OTHER PUBLICATIONS

International Preliminary Report on Patentability dated Jan. 16, 2018, in International Application No. PCT/US16/42225, 7 pages.
(Continued)

*Primary Examiner* — Camtu T Nguyen
(74) *Attorney, Agent, or Firm* — Liang IP, PLLC

(57) ABSTRACT

Treatment systems, devices, articles, and associated methods of operation for treating open wounds are disclosed herein. In one embodiment, a method includes applying a first material and a second material to be in contact with a surface of the open wound having a water content at the surface and applying a voltage differential to the first and second materials, thereby producing hydrogen peroxide ($H_2O_2$) at the surface via an electrochemical reaction between oxygen ($O_2$) in air and water ($H_2O$) in the water content at the surface. The voltage differential is calibrated
(Continued)

to correspond to a concentration of the produced hydrogen peroxide in the water content effective in reducing or preventing a bacterial infection at the surface of the open wound.

16 Claims, 19 Drawing Sheets

(51) Int. Cl.
    *A61N 1/04*     (2006.01)
    *A61N 1/20*     (2006.01)
    *A61N 1/30*     (2006.01)
    *A61L 2/18*     (2006.01)
    *A61N 1/378*     (2006.01)

(52) U.S. Cl.
    CPC ............ *A61N 1/0468* (2013.01); *A61N 1/20* (2013.01); *A61N 1/205* (2013.01); *A61N 1/30* (2013.01); *A61N 1/3782* (2013.01)

(58) Field of Classification Search
    CPC .. A61N 1/0428; A61N 1/3782; A61N 1/0436; A61N 1/0448; A61N 1/0444; A61N 1/044; A61N 1/0432; A61N 1/325; A61N 1/30; A61N 1/303; A61N 1/306; A61F 2013/00961; A61F 2013/0097
    See application file for complete search history.

(56) References Cited

U.S. PATENT DOCUMENTS

| | | | |
|---|---|---|---|
| 2006/0287632 A1* | 12/2006 | Sarangapani | ............ C25B 1/04 604/304 |
| 2009/0048651 A1* | 2/2009 | Andino | ................ A61N 1/0468 607/115 |
| 2012/0089232 A1 | 4/2012 | Choi | |
| 2013/0092531 A1 | 4/2013 | Norton et al. | |
| 2015/0025479 A1 | 1/2015 | Davis et al. | |

FOREIGN PATENT DOCUMENTS

| | | |
|---|---|---|
| WO | WO9831420 A1 | 7/1998 |
| WO | WO2004064881 A1 | 8/2004 |
| WO | 2014188070 | 11/2014 |

OTHER PUBLICATIONS

International Search Report and Written Opinion dated Oct. 5, 2016, in International Application No. PCT/US16/42225, 10 pages.
Extended European Search Report dated Feb. 11, 2019, in European Application No. 16825160.1, 9 pages.

* cited by examiner

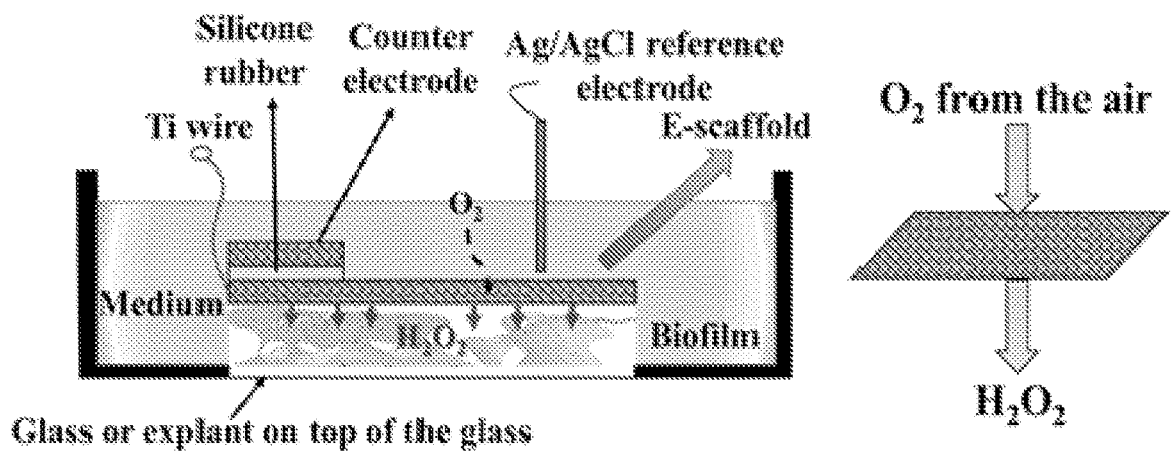
*FIG. 3*
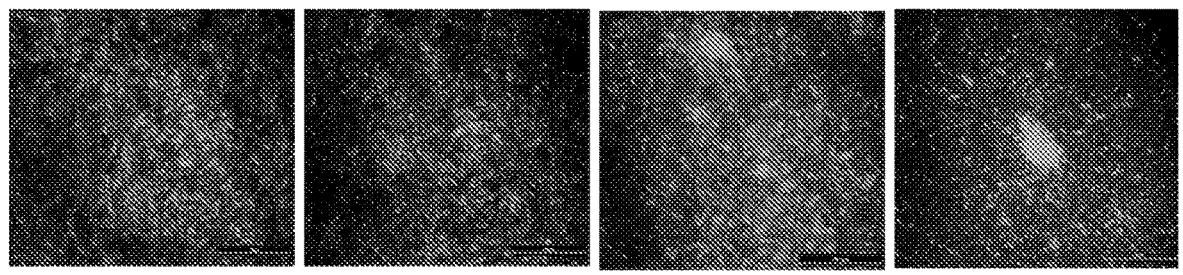
*FIG. 5A*  *FIG. 5B*
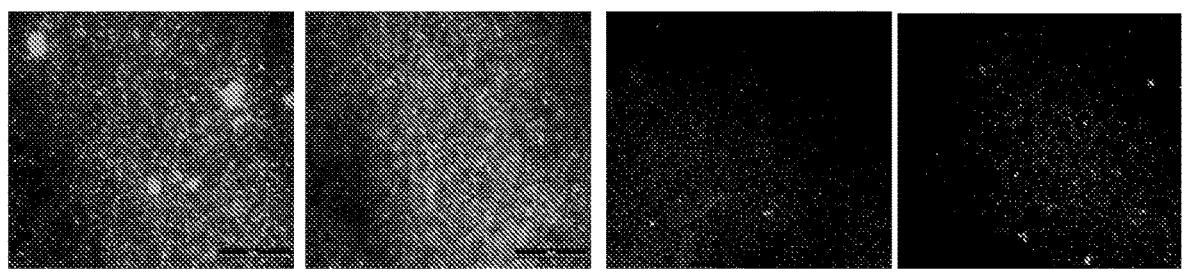
*FIG. 5C*  *FIG. 5D*

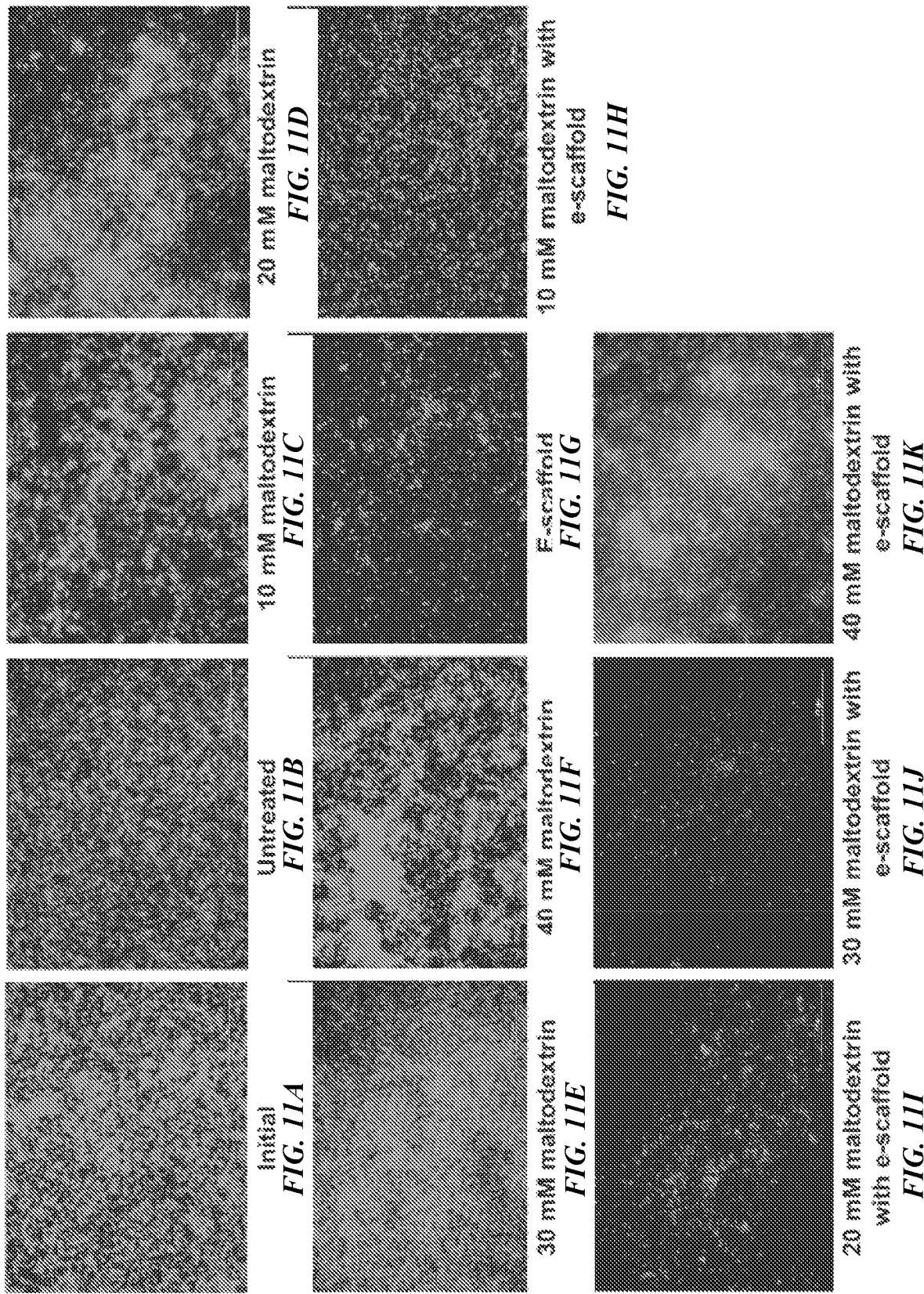

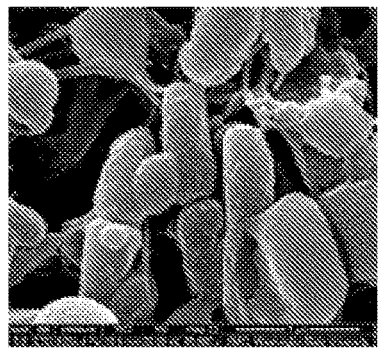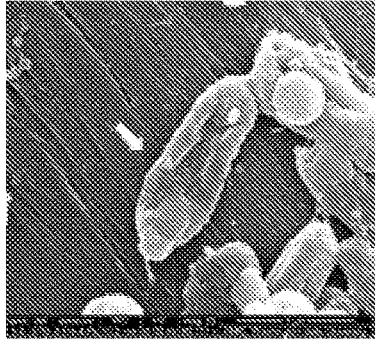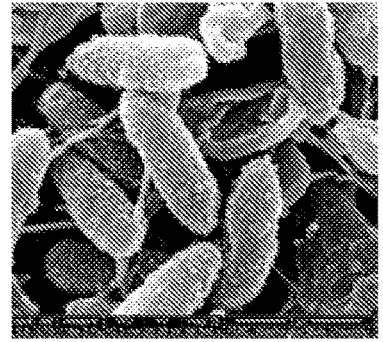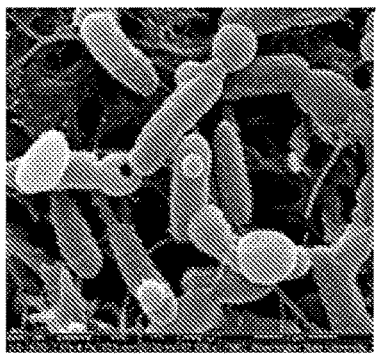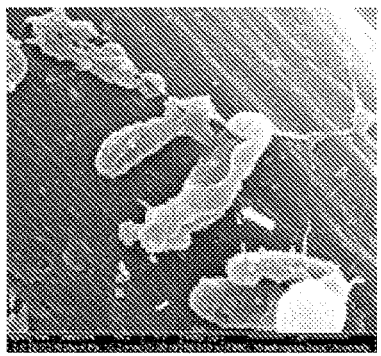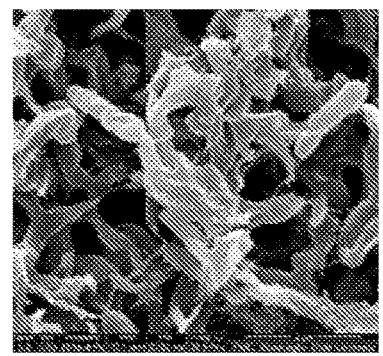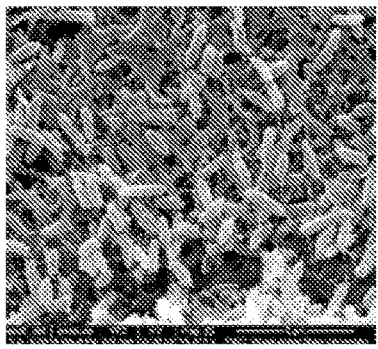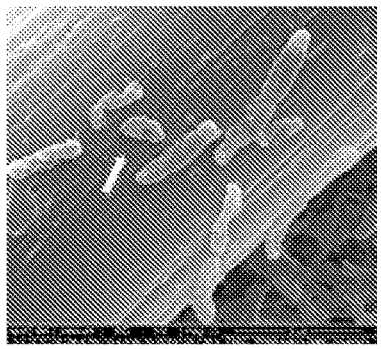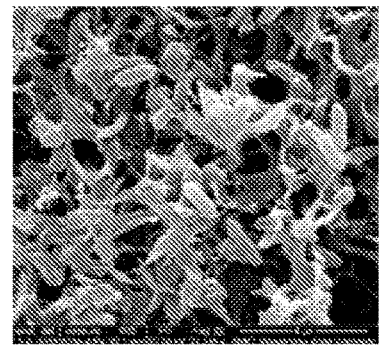
*FIG. 19A*  *FIG. 19B*  *FIG. 19C*

ELECTROCHEMICAL REDUCTION OR PREVENTION OF INFECTIONS

CROSS-REFERENCE TO RELATED APPLICATION(S)

This application claims priority to U.S. Provisional Application No. 62/192,164, filed on Jul. 14, 2015, and 62/311,747, filed on Mar. 22, 2016.

STATEMENT REGARDING FEDERALLY SPONSORED RESEARCH

This work was supported by NSF-CAREER award No. 0954186 and grant No. DM110308 from the US Department of Defense. The government has certain rights in this work.

BACKGROUND

Antibiotic-resistant organisms, e.g., *Acinetobacter baumannii*, can form a biofilm on a wound surface. The biofilm can delay healing of a wound and cause chronic wound infections because the biofilm can at least partially protect organisms in the biofilm from antibiotics. Conventional dressings loaded with antibiotics (e.g., silver, zinc, iodine, or honey) may be ineffective in reducing or removing such biofilms because the biofilms can form a diffusion barrier for the antibiotics in the dressings. Also, conventional dressings loaded with antibiotics lose potency over time as the initial load of antibiotics diminishes.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Bacteria or other organisms in biofilms can be difficult to remove from wound surfaces because biofilms can form a diffusion barrier for topically applied antibiotics. Several embodiments of the disclosed technology are directed to dressings or other suitable types of wound-treating articles that can continuously deliver antimicrobial agents (e.g., hydrogen peroxide) at desired concentrations for substantial lengths of time (e.g., hours, days, or even weeks) in order to reduce or remove biofilms from wound surfaces. In certain embodiments, a dressing in accordance with disclosed technology can include a first material electrically insulated from a second material. A power source (e.g., a battery) can be configured to electrically bias the first and second materials at a calibrated voltage difference. Under the influence of the applied voltage, a desired concentration of hydrogen peroxide can be produced at a wound surface via an electrochemical reaction of oxygen in air and water on the wound surface.

The inventors have recognized that such electrochemical reaction can produce sufficient hydrogen peroxide to reduce, if not eliminate, biofilms on the wound surface caused by organisms such as, for example, *Acinetobacter baumannii*. In other embodiments, the dressing can also include a voltage controller and an optional voltage sensor. The voltage controller can be configured to adjust the applied voltage differential between the first and second materials to achieve the desired concentration of produced hydrogen peroxide. In further embodiments, the dressing can also include a voltage or current sensor configured to monitor differential hydrogen peroxide level, a hypochlorous acid (HOCl) level, a moisture level, or a current flowing between the first and second materials, respectively.

BRIEF DESCRIPTION OF THE DRAWINGS

FIG. 3 is a schematic cross-sectional diagram of an experimental setup configured to study production of hydrogen peroxide in accordance with embodiments of the disclosed technology.

FIG. 4A shows a plot of a hydrogen peroxide concentration at about 50 μm from a polarized e-scaffold surface at potentials ranging from about +400 $mV_{Ag/AgCl}$ to about −800 $mV_{Ag/AgCl}$. The dashed line shows a current derived from linear sweep voltammetry spectra of the e-scaffold at a scan rate of 10 mV/s.

FIG. 4B shows hydrogen peroxide depth profiles for both non-polarized (control) and polarized e-scaffold surfaces. X-axis in FIG. 4B represents a distance of a microelectrode tip of a hydrogen peroxide sensor from an e-scaffold surface towards the bulk, with "0" being the surface of the e-scaffold.

FIGS. 5A-5D show images of biofilms treated under various conditions during experiments using the using the experimental setup in FIG. 3 in accordance with embodiments of the disclosed technology. In particular, FIGS. 5A-5D show *Acinetobacter baumannii* biofilms grown in vitro for 1 day [initial (t=0 hour)] and after application of e-scaffolds for 24 hours. The controls include biofilms with non-polarized e-scaffolds. Two example images are presented for each condition.

FIGS. 11A-11K are images of an *S. aureus* biofilm grown for 1 day under various test conditions using an e-scaffold and maltodextrin (MD). Concentrations tested were 36 mg/mL MD (10 mM), 72 mg/mL MD (20 mM), 108 mg/mL MD (30 mM) and 144 mg/mL MD (40 mM).

FIGS. 19A-19C are scanning electron microscopy (SEM) images showing untreated, e-scaffold treated, and exogenous H2O2 treated *P. aeruginosa* PAO1 biofilm cells, respectively, in accordance with embodiments of the disclosed technology.

DETAILED DESCRIPTION

Figure 1:
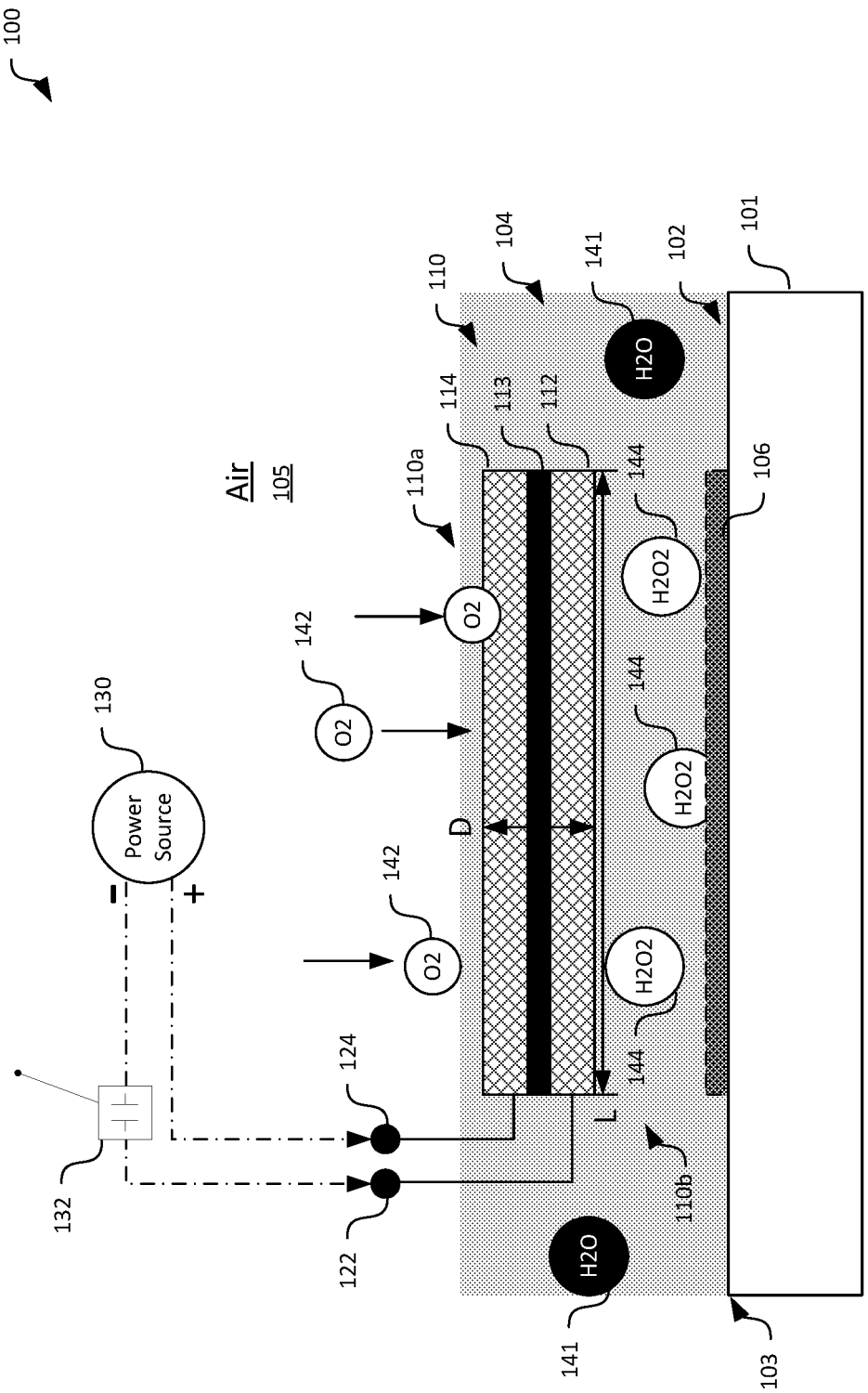
FIG. 1 is a schematic cross-sectional diagram of a treatment system for treating an open wound in accordance with embodiments of the disclosed technology.

Certain embodiments of systems, devices, articles of manufacture, and processes for delivering antimicrobial agents to a wound surface are described below. In the following description, specific details of components are included to provide a thorough understanding of certain embodiments of the disclosed technology. A person skilled in the relevant art will also understand that the disclosed technology may have additional embodiments or may be practiced without several of the details of the embodiments described below with reference to FIGS. 1-22.

As used herein, the term "dressing" generally refers to a sterile article of manufacture that can be applied to an open wound for stemming bleeding, absorbing exudate, easing pain, debriding the open wound, promoting healing, and/or reducing or preventing infections. In certain embodiments, a dressing can include a sterile pad, compress, gauze, mat, pack, or other suitable antibacterial component configured to be in direct contact with an open wound. In other embodiments, the dressing can also include a bandage, adhesive tape, or other suitable types of support component configured to support and/or integrated with the antibacterial component. In further embodiments, the dressing can further include one or more power sources, voltage/current controllers, voltage/current sensors, and/or other suitable electrical/mechanical components. In yet further embodiments, the dressing can also include a water component (e.g., a saline or antibiotic solution) in contact with and at least partially submerging the antibacterial component.

Also used herein, the term "open wound" generally refers to an injury to a human or animal body causing a damage to epidermis, dermis, cutaneous tissues, and/or subcutaneous tissues of the human or animal body. An open wound may be classified based on causes of the wound, such as, for example, incisions, lacerations, abrasions, avulsions, punctures, penetrations, gunshots, burns, or other mechanisms that can cause damages to skin and/or tissue. An open wound can have a wound surface exposed to air. A human or animal body having an open wound may secrete or excrete intracellular fluid (i.e., cytoplasmic matrix) and/or interstitial fluid (e.g., blood or lymph) at the wound surface. The secreted or excreted fluids can include a water component.

Biofilms caused by bacteria or other organisms can be difficult to remove from wound surfaces because the biofilms can form a diffusion barrier for topically applied antibiotics. Several embodiments of the disclosed technology are directed to dressings (referred to below as "e-scaffolds") that are configured to continuously deliver antimicrobial agents (e.g., hydrogen peroxide) at target concentrations for a substantial length of time via electrochemical reactions. The produced antimicrobial agents can thus reduce or even remove biofilms from wound surfaces. Particular examples of such dressings are described below with reference to FIGS. 1 and 2. In other embodiments, the dressings or other suitable types of wound-treating articles can have additional and/or different components or structures.

E-Scaffold

FIG. 1 is a schematic cross-sectional diagram of a treatment system 100 for treating an open wound 102 in accordance with embodiments of the disclosed technology. In the following description, embodiments of the treatment system 100 can also be referred to as "electrochemical scaffolds" or "e-scaffolds." As shown in FIG. 1, the dressing 110 can include a first material 112, a second material 114, and an insulation material 113 between the first and second materials 112 and 114. The dressing 110 can also include a first electrode 122 and a second electrode 124 coupled to the first material 112 and the second material 114, respectively. Even though particular components of the dressing 110 are shown in FIG. 1, in other embodiments, the dressing 110 can also include additional and/or different adhesives, sensors, and/or other suitable electrical/mechanical components.

In certain embodiments, the insulation material 113 can include a glue that binds the first and second materials 112 and 114. In other embodiments, the first material 112, the insulation material 113, and the second material 114 can be fastened together utilizing a fastener (e.g., a clip, a rivet, etc.). In yet other embodiments, the first material 112, the insulation material 113, and the second material 114 of the dressing 110 can be assembled frictionally, electrostatics, or via other suitable mechanisms. In the illustrated embodiment of FIG. 1, the first material 112, the insulation material 113, and the second material 114 are shown as having certain depths D and lengths L, in other embodiments, the foregoing parts of the dressing 110 can have different depths, lengths, and/or other suitable sizes.

In certain embodiments, the first material 112 and the second material 114 can individually include a fabric constructed from an electrically semi-conductive or conductive material. For example, the first and second materials 112 and 114 can individually include a carbon fabric, a metallic mesh, an alloy mesh, or other suitable materials. In other embodiments, the first and second materials 112 and 114 can also include sheets, foils, or other suitable structures constructed and/or embedded with an electrically semi-conductive or conductive material.

The insulation material 113 can include an electrically insulating material configured to insulate the first and second materials 112 and 114. In one example, the insulation material 113 can include a silicone rubber having an appropriate size between the first and second materials 112 and 114. In other embodiments, the insulation material 113 can include polymeric or other suitable electrically non-conductive materials. In further embodiments, the insulation material 113 can include an air gap, an ion or proton exchange membrane, or other suitable insulation materials between the first and second materials 112 and 114.

The first material 112, the insulation material 113, and the second materials 114 can be at least partially gas permeable. For instance, as shown in FIG. 1, the first material 112, the insulation material 113, and the second materials 114 can allow air (approximately 79% Nitrogen and 21% oxygen) to permeate through the dressing 110 from a first side 110a to a second side 110b proximate a wound surface 103 of a human or animal body 101. In other examples, the first material 112, the insulation material 113, and the second materials 114 can also allow a gas with enriched oxygen (e.g., with a concentration greater than 21%) to permeate through the dressing 110 from the first side 110a to the second side 110b.

As shown in FIG. 1, the first and second electrodes 122 and 124 can be electrically coupled to first and second polarities of a power source 130 via an optional switch 132. In one embodiment, the power source 130 can include a battery having a target voltage differential (e.g., about 0.6 volts). In other embodiments, the power source 130 can also include a solar cell, a fuel cell, or other suitable direct current power sources. In the illustrated embodiment, the first electrode 122 is coupled to the negative polarity and the second electrode 124 is coupled to the positive polarity of the power source 130. In other embodiments, the first and second electrodes 122 and 124 can also have other suitable relative polarities. Even though the power source 130 is shown as a separate component from the dressing 110, in certain embodiments, the power source 130 can be provided as an integrated part of the dressing 110. In other embodiments, the power source 130, the dressing 110, and/or other components of treatment system 100 can be provided as a kit with instruction literatures for application of the dressing 110 as described below.

As shown in FIG. 1, the body 101 can include a wound 102 having a wound surface 103 and a biofilm 106 that may be formed at or proximate the wound surface 103. The body 101 can also have blood, lymph, cytoplasmic matrix, or other water content 104 on the wound surface 103. During treatment, the dressing 110 can be placed with the first material 112 proximate the wound surface 103 and the second material 114 proximate air 105. In FIG. 1, the first material 112 is shown as spaced apart from the biofilm 106 and the wound surface 103 for illustration purposes. The second material 114 is shown as submerged in the water content 104. In other embodiments, the first material 112 can be at least partially in physical contact with the biofilm 106 and/or the wound surface 103, and the second material 114 can be at least partially exposed to air 105.

Output of the power source 130 can be coupled to the first and second electrodes 122 and 124. In one embodiment, the optional switch 132 can then be activated to allow the power source 130 to bias the first and second materials 112 and 114 via the first and second electrodes 122 and 124, respectively, at a target voltage differential. Without being bound by theory, it is believed that the applied voltage differential between the first and second materials 112 and 114 can cause an electrochemical reaction between water ($H_2O$) 141 in the water content 104 and oxygen ($O_2$) 142 trapped in the dressing 110 or permeating from air 110 through the dressing 110 to produce hydrogen peroxide ($H_2O_2$) 144 as follows:

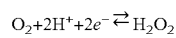

The produced hydrogen peroxide can be at a target concentration sufficient to oxidize and thus reduce or even eliminate the biofilm 106 at the wound surface 103 of the body 101.

Several embodiments of the dressing 110 can be more effective than conventional dressings in controlling or eliminating biofilms. Unlike conventional dressings that lose potency with diminishing antimicrobial concentration over time, embodiments of the dressing 110 can be configured to provide a generally constant concentration of hydrogen peroxide at or near the wound surface 103. As described in more detail below with reference to the Experiment section, such prolonged exposure to hydrogen peroxide can effectively control or even eliminate biofilms, and thus promote healing of the wound.

Even though the dressing 110 is shown in FIG. 1 as being placed in air 105, in other embodiments, at least a part of the dressing 110 may also be placed in an oxygen-enriched atmosphere, by, for example, supplying a gas containing about 95% oxygen to the wound 102. In other embodiments, an aqueous fluid (e.g., sterile water or saline solution) may be provided at the wound surface to provide the water content 104. In yet further embodiments, additional electrolyte solution (e.g., saline) may also be continuously or periodically provided to the wound 102 to maintain a moist environment at the wound surface 103. In other embodiments, the treatment system 100 can also include additional and/or different components, as described below with reference to FIG. 2. In further embodiments, the dressing 110 can also be pre-loaded or combined during treatment with sodium chloride (NaCl), potassium chloride, or other suitable chlorine containing compounds, as described in more detail below with reference to FIGS. 21A-22.

Figure 2:
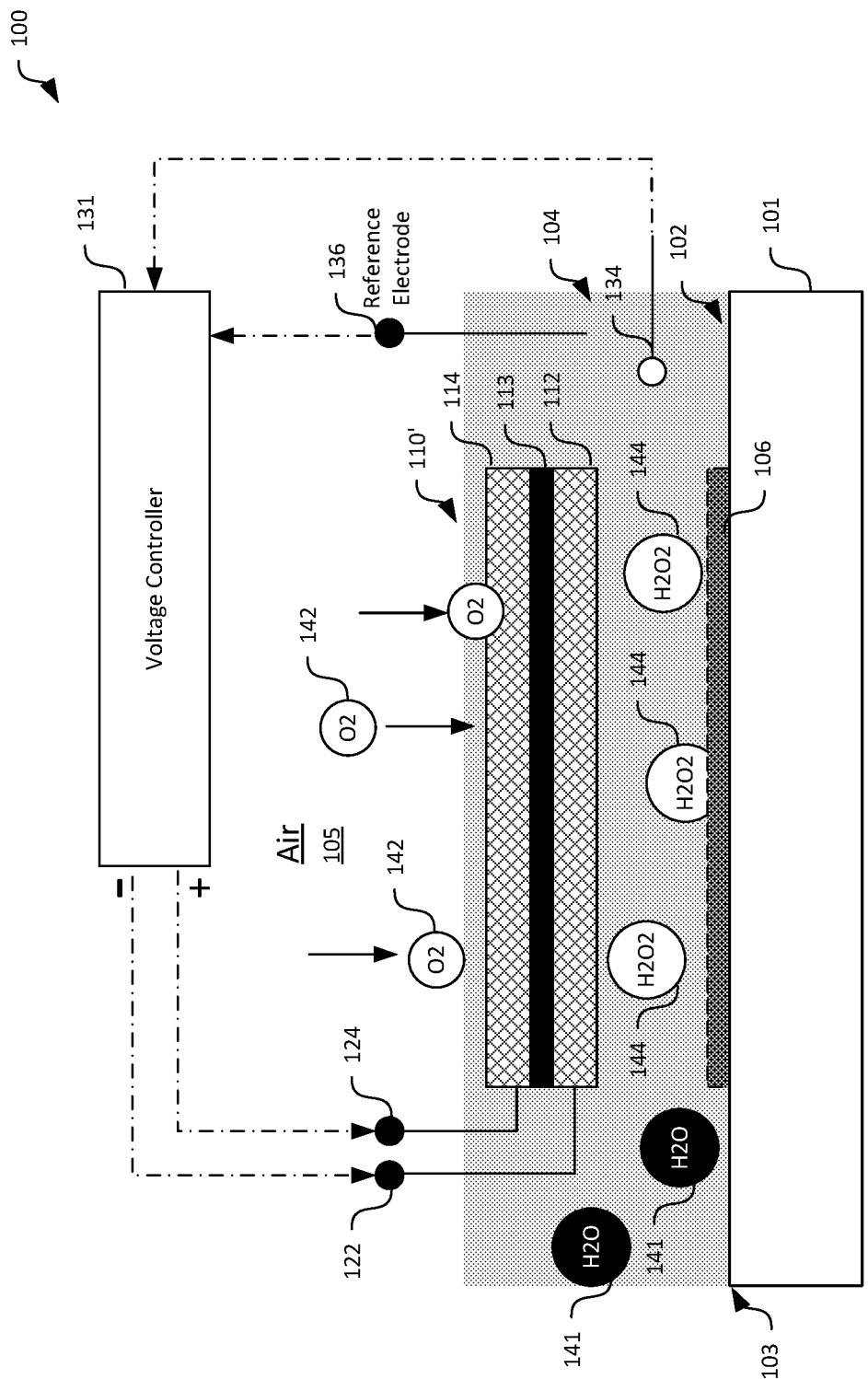
FIG. 2 is a schematic cross-sectional diagram of another treatment system for treating an open wound in accordance with embodiments of the disclosed technology.

FIG. 2 is a schematic cross-sectional diagram of another treatment system 100' for treating an open wound 102 in accordance with embodiments of the disclosed technology. The treatment system 100' shown in FIG. 2 can include certain components generally similar in structure and function as those shown in FIG. 1. As such similar components are identified with similar references.

As shown in FIG. 2, the treatment system 100' can include the dressing 110 with the first material 112, the insulation material 113, and the second material 114. The first and second materials 112 and 114 can be electrically coupled to first and second electrodes 122 and 124, respectively. However, unlike the treatment system 100 of FIG. 1, the treatment system 100' can include a voltage controller 131 with output electrically coupled to the first and second electrodes 122 and 124 for biasing the first and second materials 112 and 114.

As shown in FIG. 2, the voltage controller 131 can cooperate with the first and second electrodes 122 and 124 and a reference electrode 136 placed in the water content 104 to achieve a target voltage differential between the first and second materials 112 and 114. In one embodiment, the voltage controller 131 can include a potentiostat. In other embodiments, the voltage controller 131 can include other suitable hardware/software for controlling an applied voltage differential between the first and second materials 112 and 114.

The reference electrode 136 can include an electrode that has a stable and well-known electrode potential. For example, in one embodiment, the reference electrode 136 can include a standard hydrogen electrode with a potential E=0.000 V at an activity of H$^+$=1. In other embodiments, the reference electrode 136 can also include a normal hydrogen electrode, a reversible hydrogen electrode, a saturated calomel electrode, a copper-copper (II) sulfate electrode, a silver chloride electrode, a pH electrode, a palladium-hydrogen electrode, a mercury-mercurous sulfate electrode, or other suitable types of reference electrode.

Optionally, in certain embodiments, the treatment system 100' can also include a hydrogen peroxide sensor 134 placed proximate the wound surface 102. The hydrogen peroxide sensor 134 can be configured to measure a concentration of hydrogen peroxide proximal to the wound surface 102. In one example, the hydrogen peroxide sensor can include a microelectrode. In other embodiments, the hydrogen peroxide sensor can include other suitable components.

In operation, the voltage controller 131 can adjust and/or maintain an applied voltage differential to the first and second materials 112 and 114 based on the measured voltage differential with reference to input from the reference electrode 136. In one embodiment, the voltage controller 131 can receive a user input of a setpoint voltage differential and adjust the applied voltage differential to achieve the setpoint voltage differential. In other embodiments, the voltage controller 131 can adjust the applied differential based on a calibration of concentration of produced hydrogen peroxide versus the applied voltage differential. In yet further embodiments, the voltage controller can receive a user input of a setpoint concentration of the produced hydrogen peroxide. The voltage controller can then adjust the applied differential to achieve the setpoint concentration of the produced hydrogen peroxide based on an input from the hydrogen peroxide sensor 134.

E-Scaffold Experiments

Experiments were conducted to (1) develop electrochemical articles (referred to herein as "e-scaffold") that can reduce atmospheric oxygen to hydrogen peroxide; (2) test biocidal efficacy of e-scaffold at eliminating biofilms from *Acinetobacter baumannii* grown in vitro and on porcine explant models; and (3) use an explant model to determine whether the e-scaffold damages underlying tissue. As described below, a continuous (40 hours) electrochemical generation of low concentrations of hydrogen peroxide ($H_2O_2$) was detected near a stainless steel electrode with negative polarity and that the hydrogen peroxide appeared to delay biofilm development. It is believed that the electrochemical formation of hydrogen peroxide is resulted from a partial reduction of dissolved oxygen in an aqueous fluid as per equation (1) below:

$$O_2 + 2H^+ + 2e^- \rightleftarrows H_2O_2 (\Delta E^{0'} = +85 mV_{Ag/AgCl}) \tag{1}$$

The standard reduction potential of hydrogen peroxide is about +85 $mV_{Ag/AgCl}$, but due to activation over-potential, hydrogen peroxide production usually accompanies negative polarization potentials. When an electrode in a wound environment is polarized below +85 $mV_{Ag/AgCl}$, oxygen can be reduced to generate hydrogen peroxide, which can prevent/delay biofilm growth. As used herein, the term "polarized" refers to a state in which a voltage differential is applied. Depending on concentration, the electrochemical generation of hydrogen peroxide can be compatible with wound healing because a low concentration of hydrogen peroxide is normally produced in wounds as a cellular inflammatory response. A low concentration of hydrogen peroxide can avoid oxidative damages to tissues. Also, such electrochemical generation of hydrogen peroxide can be continuous over time. Thus, electrochemical articles configured to continuously provide controlled delivery of a low concentration of hydrogen peroxide can function as an efficient antibiotic-free wound dressing to reduce or even eliminate biofilms.

FIG. 3 is a schematic cross-sectional diagram of an experimental setup configured to study production of hydrogen peroxide in accordance with embodiments of the disclosed technology. As shown in FIG. 3, carbon-based conductive fabric was used as e-scaffold material. Such carbon-based fabric possesses biological compatibility, flexibility, and has been used as both electrodes and wound dressing material. Polarized e-scaffold was overlaid onto an *Acinetobacter baumannii* biofilm for 24 hours. Afterwards, changes in biofilm surface coverage were quantified from biofilm images and the colony-forming units were counted.

To verify that electrochemical generation of hydrogen peroxide was the dominant mechanism for biofilm reduction/elimination, externally added catalase was used to decompose hydrogen peroxide generated by an e-scaffold in another *Acinetobacter baumannii* biofilm. Similarly, in a separate experiment, hydrogen peroxide was added at concentrations experimentally observed by the e-scaffold to confirm that hydrogen peroxide was responsible for reducing or even eliminating *Acinetobacter baumannii* biofilm. An e-scaffold was further tested against infected porcine explants.

Electrochemical Scaffold (e-Scaffold) Examples

As shown in FIG. 3, the e-scaffold was constructed to include a working electrode, a counter electrode, and a reference electrode. The working electrode was configured to hold a negative polarity to reduce oxygen and generate hydrogen peroxide. To complete the electrochemical cell, a counter electrode and an Ag/AgCl reference electrode was used. The e-scaffold was fabricated using carbon fabric (Panex 30 PW-06, Zoltex Companies Inc., St Louis, Mo.). The fabric was cut in a circular shape (6.42 cm$^2$) to serve as the working electrode, and a smaller carbon fabric patch (2.14 cm$^2$) was used as the counter electrode. The counter electrode was attached to the working electrode using a layer (about 1 mm) of silicone rubber (Dynaflex 230 Indoor/Outdoor Sealant, catalog #18357) as an insulation material to provide electrical insulation between the working and counter electrodes while still allowing oxygen to permeate/diffuse to the working electrode for hydrogen peroxide generation.

An electric potential applied to the e-scaffold was controlled using a Gamry Series G300™ potentiostat (Gamry Instruments, Warminster, Pa., USA, not shown in FIG. 3) with the Ag/AgCl reference electrode. Titanium wires (0.025 Titanium, Malin Co., Cleveland, Ohio, Lot #27567) were used to connect the electrode ends to the external cables leading to the potentiostat. The connection resistance was consistently less than about 2Ω. The e-scaffold was overlaid either onto biofilms grown in vitro on glass surface or onto infected or uninfected porcine explants, as shown in FIG. 3. This configuration allowed the ventral surface of the e-scaffold to be exposed directly to biofilms.

Quantifying $H_2O_2$ Production from e-Scaffold

Hydrogen peroxide production was quantified by coupling both linear sweep voltammetry and constant polarization of the e-scaffold with direct measurement of $H_2O_2$ using a $H_2O_2$ microelectrode. Initially, the microelectrode tip (<20 μm) was positioned above the e-scaffold (~1000 μm) using a precision linear actuator (PI M-230.10S, Physik Instrumente, Auburn, Mass., USA). The microelectrode tip and the e-scaffold surface were located using a stereomicroscope (Zeiss Stemi 2000). The microelectrode tip was then moved down to within about 50 μm of the e-scaffold surface. At this position, linear sweep voltammetry was initiated from +400 mV$_{Ag/AgCl}$ to −800 mV$_{Ag/AgCl}$ at 10 mV/s. The onset of $H_2O_2$ production was measured from this voltammetry, and −600 mV$_{Ag/AgCl}$ was selected as a target potential to produce $H_2O_2$ near the surface.

Following linear sweep voltammetry, the e-scaffold was polarized to −600 mV$_{Ag/AgCl}$ and a current was allowed to reach a steady state value. Starting at 1000 μm from the e-scaffold surface, the microelectrode tip was stepped down in 5-μm increments towards the e-scaffold surface. After each increment the $H_2O_2$ concentration was measured to develop a depth-resolved concentration profile. The accumulation of $H_2O_2$ at the e-scaffold surface and the penetration distance into the bulk were measured using these depth profiles. The depth profile of $H_2O_2$ for a non-polarized e-scaffold surface was similarly measured as a control.

Growing In Vitro Biofilms

*Acinetobacter baumannii* biofilms were used to test efficacy of the e-scaffold. An overnight culture of *Acinetobacter baumannii* (ATCC #BAA-1605) was grown in full-strength Luria Broth (LB) medium (Sigma-Aldrich, catalog #L3522) and was re-suspended in 5% LB medium (OD$_{600}$≈0.5). For imaging experiments, green fluorescent protein (GFP) expressing *Acinetobacter baumannii* (ATCC #17978) was used and LB medium was supplemented with ampicillin (100 μg/mL; Sigma-Aldrich, catalog #A5354-10ML). Sterile glass bottom petri dishes (MatTek Corporation, catalog #P35G-1.5-20-C) were used to grow and image the biofilms. After 2 hours of initial attachment, the bacterial suspension was removed and the biofilms were washed twice to remove planktonic cells and then refreshed with 5% LB medium. Biofilms were allowed to develop for 24 hours. Before the e-scaffolds were applied, the bulk liquid was refreshed.

Application of e-Scaffold to In Vitro Biofilms

E-scaffolds were sterilized by autoclaving (121° C., 15 min) and were saturated with sterilized liquid medium before being applied to existing *Acinetobacter baumannii* biofilms. The scaffolds were then polarized at −600 mV$_{Ag/AgCl}$ for 24 hours, after which biofilms were processed for the quantification of viable cells by scraping the e-scaffold and biofilms from the glass surfaces of the petri dish into 5 ml of LB medium (1 g/L). The suspensions were centrifuged, and the resulting cell pellet was re-suspended in 1 ml of LB medium (1 g/L), and serial dilutions were prepared. Colony-forming units ("CFU") were counted using a drop-plate count method. Biofilms exposed to non-polarized e-scaffolds were used as a control.

Biofilm Imaging and Analysis

An inverted epi-fluorescence microscope (Nikon Eclipse Ti-S inverted microscope) with a Nikon DS-Qi1Mc camera and a CFI Plan Fluor ELWD 40× objective (N.A. 0.60, W.D. 3.72.7 mm) was used to image the cells. Biofilms were imaged before exposure to the e-scaffold (t=0 hour) and after 24 hours of exposure. To remove any planktonic cells, biofilms were washed twice and refreshed with 5% LB medium supplemented with ampicillin prior to imaging. Image Structure Analyzer ("ISA") was used to calculate surface coverage by biomass from the digitized biofilm images automatically. At least ten discrete images were taken each time to obtain statistically representative data. Average values were calculated for these ten images. The average values of three biological replicates were used to calculate the means and standard errors. Surface coverage, which is the ratio of the area of the biomass to the total area of the image, was used as a main indicator of biofilm structure. The higher the percentage surface coverage, the higher the coverage of the glass surface by biofilms.

External H$_2$O$_2$ Addition

To test whether H$_2$O$_2$ can remove biofilms in vitro and from infected porcine explants, exogenous H$_2$O$_2$ (VWR, Catalog #RC3819-16, adjusted to a concentration similar to that produced by the e-scaffold) was added to *Acinetobacter baumannii* biofilms. The total amount of H$_2$O$_2$ generated from the e-scaffold was estimated by charge balance calculations from equation (1) above and the integration of current vs. time data observed from the potentiostat. First, the biofilms were exposed to the total calculated amount of H$_2$O$_2$ in a single administration. Then, in separate experiments, H$_2$O$_2$ was added continuously (similar to the e-scaffold) to biofilms at an average of 2 mM/hour for 24 hours. Stabilizers (0.005% sodium sulfate and 0.003% manganese phosphate) was added to the solution. The stabilizers were also included in a separate control treatment.

External Catalase Addition

Catalase (Sigma-Aldrich, catalog #C1345) was added to an *Acinetobacter baumannii* biofilm and measured protection against H$_2$O$_2$ produced by the e-scaffold. Prior to addition, the H$_2$O$_2$ decomposition rate per unit of catalase was determined from H$_2$O$_2$ microelectrode measurements. The total amount of catalase required per min for complete decomposition of H$_2$O$_2$ was calculated based on the rate of H$_2$O$_2$ generation by the e-scaffold. To ensure complete H$_2$O$_2$ decomposition, catalase was added in excess of the calculated value (5×=0.05 mg/ml). In a separate experiment we tested the ability of this amount of catalase to inhibit biofilms.

Biofilm-Infected Porcine Explants

The e-scaffold was tested against biofilm-infected porcine explants. Ear tissues were harvested from domestic pigs (obtained from C & L Lockers, Moscow, Id., USA), immediately cooled to 4° C. and kept for less than an hour at this temperature before being processed. After the tissues were cleaned with 70% ethanol and hair was removed using an electric razor, skin was excised with a scalpel. For the intact epidermis model the excised skin was sectioned at a thickness of approximately 500 µm, using Padgett's dermatome, and punched into 12-mm-diameter discs, excluding skin with visible structural changes (scratches, erosion or scars). For the partial cutaneous wound model, mid-dermal sheets with a thickness of 500 µm were harvested. Skin punches with the dermal side down were used to seed polycarbonate transwell inserts (Greiner Bio-One North America, Inc., catalog #657641) with a 0.4-µm pore size membrane separating each explant from the outer well prefilled with 2 ml of cell nutrient medium. These models were maintained at 37° C. and 95% humidity in a 5% CO$_2$ environment. The nutrient medium includes a serum-free Dulbecco's Modified Eagles Medium (DMEM) (Thermo Scientific, catalog #SH3024301) supplemented with L-glutamine (0.584 g/L), ampicillin (50 µg/ml) and, antifungal amphotericin B (0.4 µg/ml). Biofilms were initiated by adding 5 µl of overnight culture of *Acinetobacter baumannii* (ATCC #17978, OD$_{600}$≈0.5) to the center of each explant surface. After 4 days the biofilm-infected porcine explants were used for experiments.

Application of e-Scaffold to Infected Porcine Explants

E-scaffolds prepared as described above were overlaid onto *Acinetobacter baumannii* biofilm-infected porcine explants. The inner well with the explant and e-scaffold was filled with 4 ml of sterile PBS as electrolyte. Similar to in vitro experiments, the e-scaffold surface exposed to biofilm was polarized at −600 mV$_{Ag/AgCl}$. Biofilms exposed to non-polarized e-scaffolds were used as a control. After 24 hours of polarization, the e-scaffolds as well as the explants with biofilms from both polarized and control wells were collected and processed for serial dilution and bacterial cell counts as described above.

Cytotoxicity Test of the e-Scaffold on Porcine Explants

The cell viability in the uninfected porcine explants with induced wounds was quantified to test whether the polarized e-scaffold treatment damaged the tissues. After application of the polarized e-scaffold for 24 hours, the porcine explant cell viability was quantified using PrestoBlue cell viability reagent (Life Technologies, catalog #A-13261). The explants were incubated in 300 µL of 10% PrestoBlue (in DMEM) for 3 hours at 37° C. in an environment with 95% humidity and 5% CO$_2$. The absorbance of the medium was then measured at 570 nm and 600 nm. The percent reduction of PrestoBlue was calculated from this absorbance and a molar extinction coefficient of oxidized and reduced PrestoBlue. PrestoBlue reduction calculated for explants exposed to polarized e-scaffolds was compared to that of the control, i.e., explants with non-polarized e-scaffolds. A normalized viability score of 100% was given to the explant showing the highest percent reduction of PrestoBlue for this control.

Figure 4A:
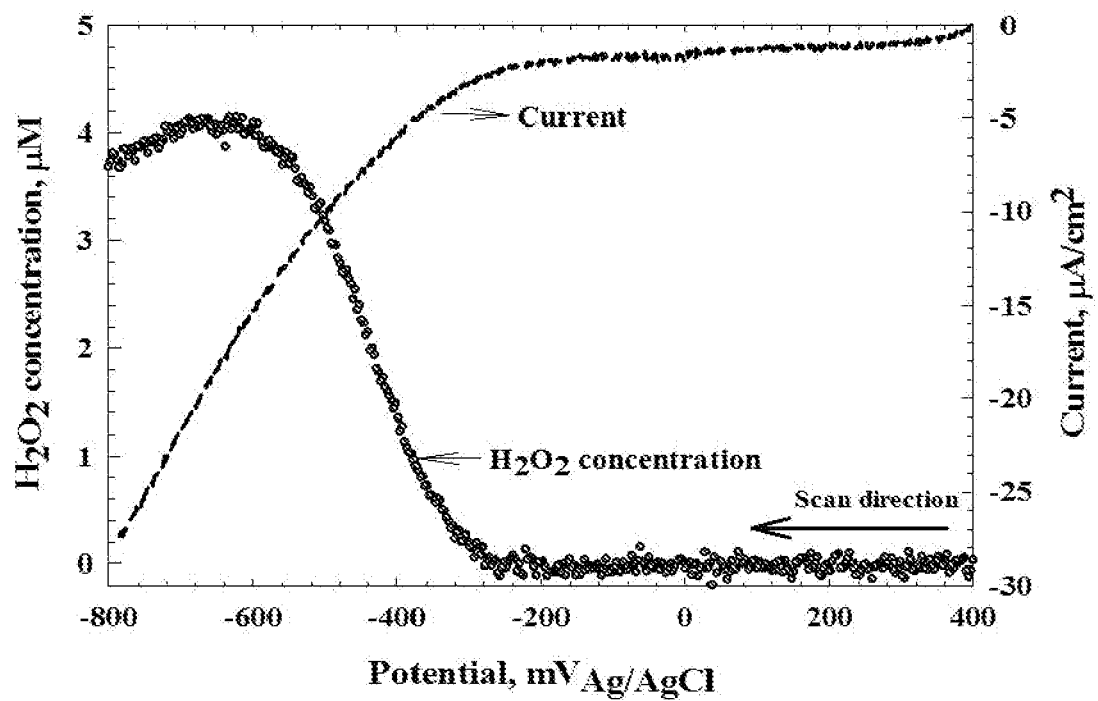
FIG. 4A is an example plot of hydrogen peroxide concentration versus applied voltage differential based on experiments using the experimental setup in FIG. 3 in accordance with embodiments of the disclosed technology. In particular.
Figure 4B:
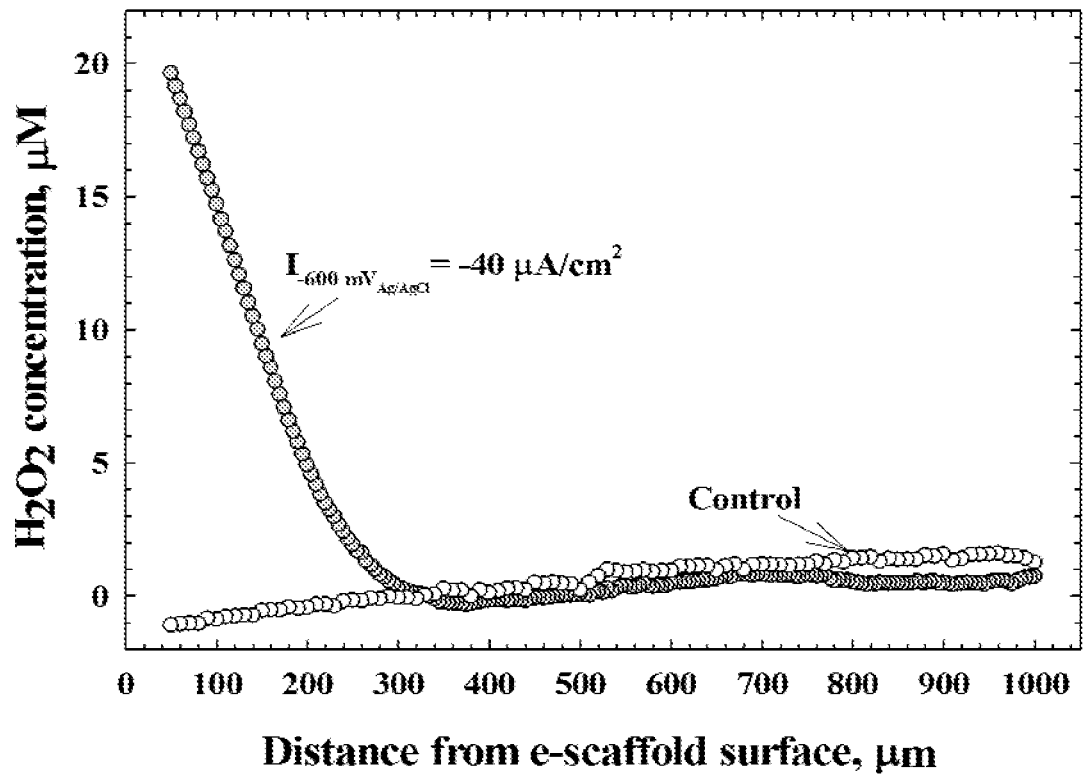
FIG. 4B is an example plot of hydrogen peroxide concentration versus a distance from a surface of a test dressing based on experiments using the experimental setup in FIG. 3 in accordance with embodiments of the disclosed technology. In particular.

Hydrogen peroxide (H$_2$O$_2$) was detectable near the e-scaffold surface when it is polarized at −300 mV$_{Ag/AgCl}$, as shown in FIG. 4A. A maximum H$_2$O$_2$ concentration was detected at −600 mV$_{Ag/AgCl}$. For all subsequent experiments the e-scaffolds were polarized at −600 mV$_{Ag/AgCl}$. Depth profile measurements demonstrated that the H$_2$O$_2$ concentration was ~25 µM at the e-scaffold surface but declined to almost zero at 300 µm from the e-scaffold surface, as shown in FIG. 4B. Such low concentrations of H$_2$O$_2$ are believed to be sufficient to promote wound healing by eliminating biofilm without damaging mammalian tissue. The non-polarized e-scaffolds produced no detectable H$_2$O$_2$, as shown in FIG. 4B.

Figure 6A:
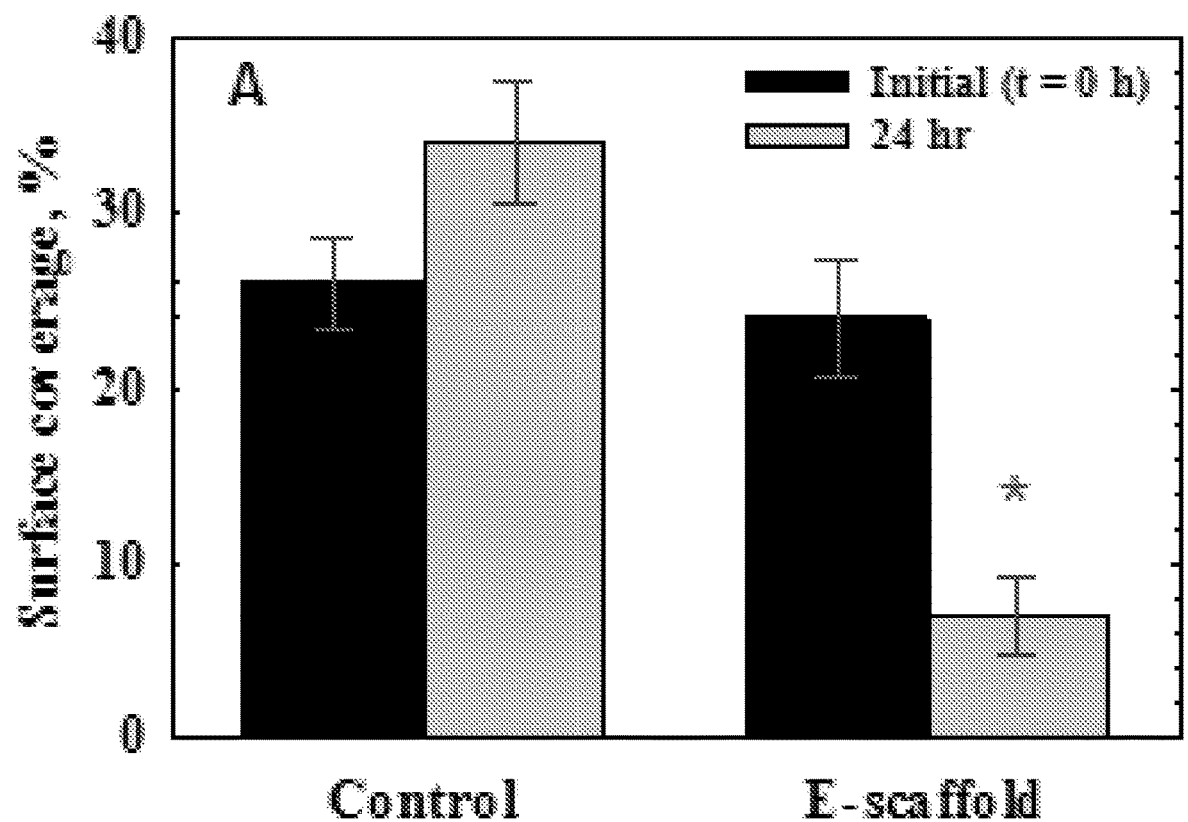
FIG. 6A is an example histogram of a surface covering percentage under various conditions during experiments using the using the experimental setup in FIG. 3 in accordance with embodiments of the disclosed technology.
Figure 6B:
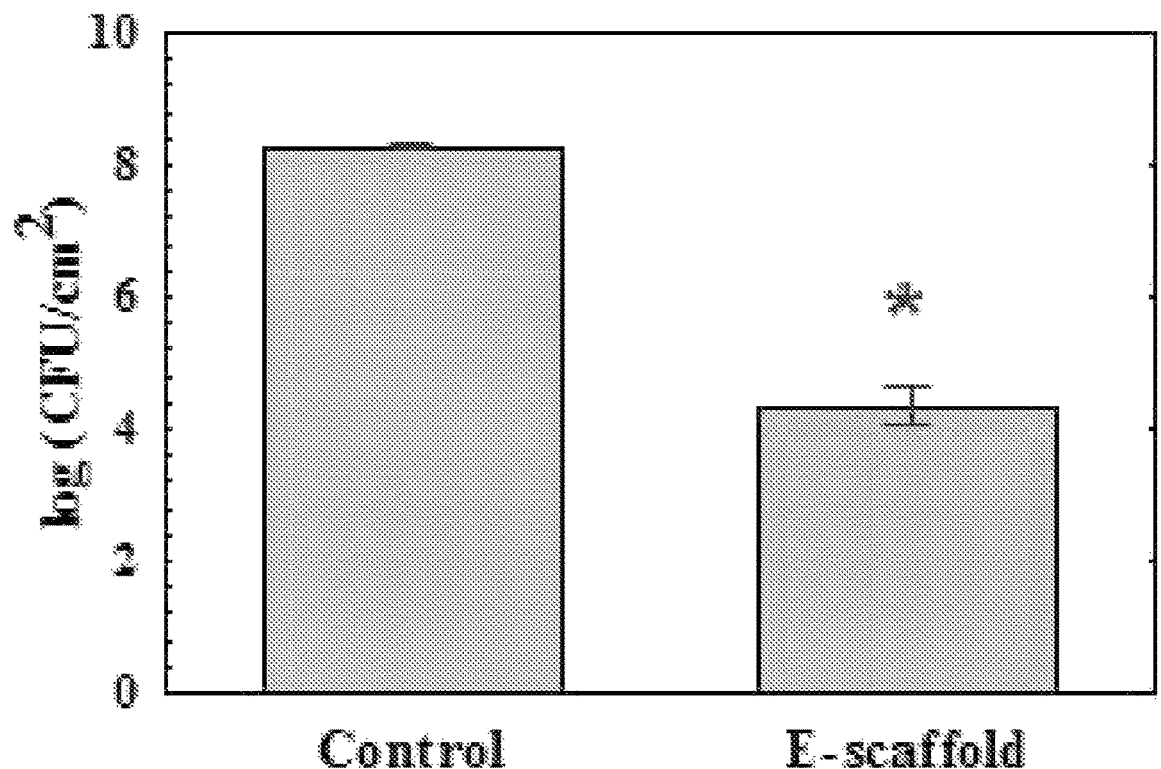
FIG. 6B is an example histogram of a biofilm reduction under various conditions during experiments using the using the experimental setup in FIG. 3 in accordance with embodiments of the disclosed technology. The symbol * denotes a significant difference compared to treatment with an e-scaffold alone (n=3 and P<0.001, one-way ANOVA with Bonferroni post hoc t-test).

FIGS. 5A-5D show example images of GFP-expressing *Acinetobacter baumannii* biofilms initially and after 24 hours for both non-polarized (control) and polarized e-scaffolds. In particular, FIG. 5A shows biofilm with non-polarized e-scaffold at time zero. FIG. 5B shows biofilm with polarized e-scaffold at time zero. FIG. 5C shows biofilm with non-polarized e-scaffold in 24 hours. FIG. 5D shows biofilm with polarized e-scaffold in 24 hours. As shown in FIG. 5C, the control biofilms continued to grow into larger biofilm clusters over a 24-hour period. In contrast, the biofilm disappeared after 24 hours of exposure to the polarized e-scaffold (FIG. 5D). After a 24-hour application of the e-scaffold, the biofilm was reduced significantly, from 25.0±2.0% to 7.0±2.3% (P<0.05), whereas the biofilm coverage increased to 34.0±3.5% for the control biofilms, as shown in FIG. 6A. The colony-forming units (log (CFU/cm$^2$) of e-scaffold-treated biofilms decreased to 4.35±0.27, and those of the control were 8.29±0.05, as shown in FIG. 6B. The amount of hydrogen peroxide generated by the e-scaffold was calculated by integrating current over time and converting the integrated total current to moles of hydrogen peroxide. This resulted in an estimate of ~45 mM hydrogen peroxide generated during a 24-hour period.

Figure 7A:
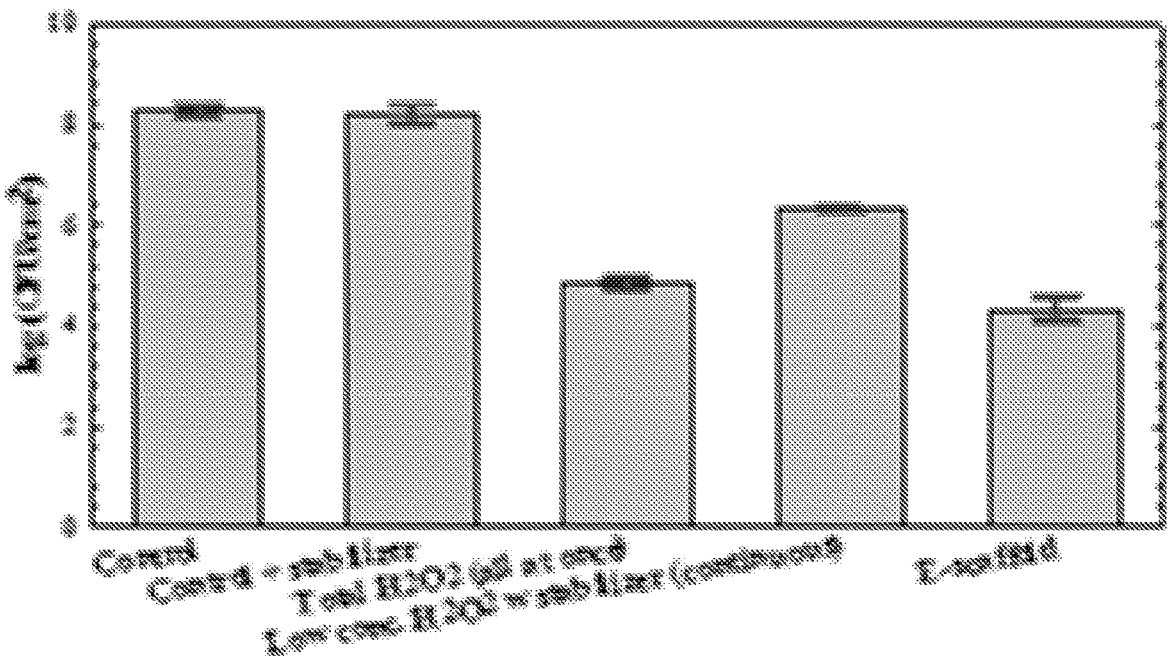
FIGS. 7A and 7B are example histograms of a biofilm reduction under various conditions during experiments using the using the experimental setup in FIG. 3 in accordance with embodiments of the disclosed technology.
Figure 7B:
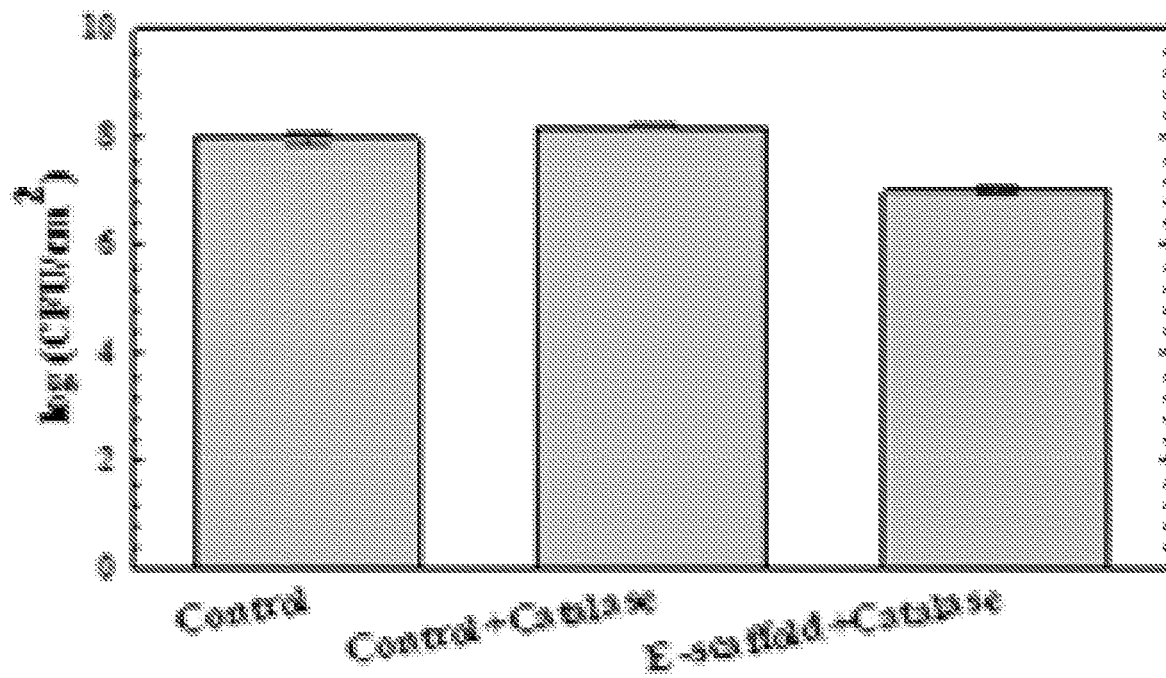

Exogenous hydrogen peroxide was added to *Acinetobacter baumannii* biofilms. When 45 mM H$_2$O$_2$ was delivered in a single administration, there was a ~3-log reduction in *Acinetobacter baumannii* CFU compared to a control without H$_2$O$_2$. This magnitude of reduction is similar to that of in situ biofilm reduction, as shown in FIG. 7A. When an equivalent concentration of H$_2$O$_2$ was delivered continuously over 24 hours, a ~2-log reduction in bacterial counts was observed, as shown in FIG. 7B. When catalyze was applied to the biofilms, the e-scaffold only produced a ~1-log reduction in the number of viable cells, and the catalase itself had no significant effect on biofilm, as shown in FIG. 7B. Because the e-scaffold reduced the number of viable cells by ~4 log as shown in FIG. 7A, and the addition of catalase blocked all but a ~1-log reduction, as shown in FIG. 7B, it is thus believed that the main biocidal activity is due to electrochemically generated $H_2O_2$.

Figure 8:
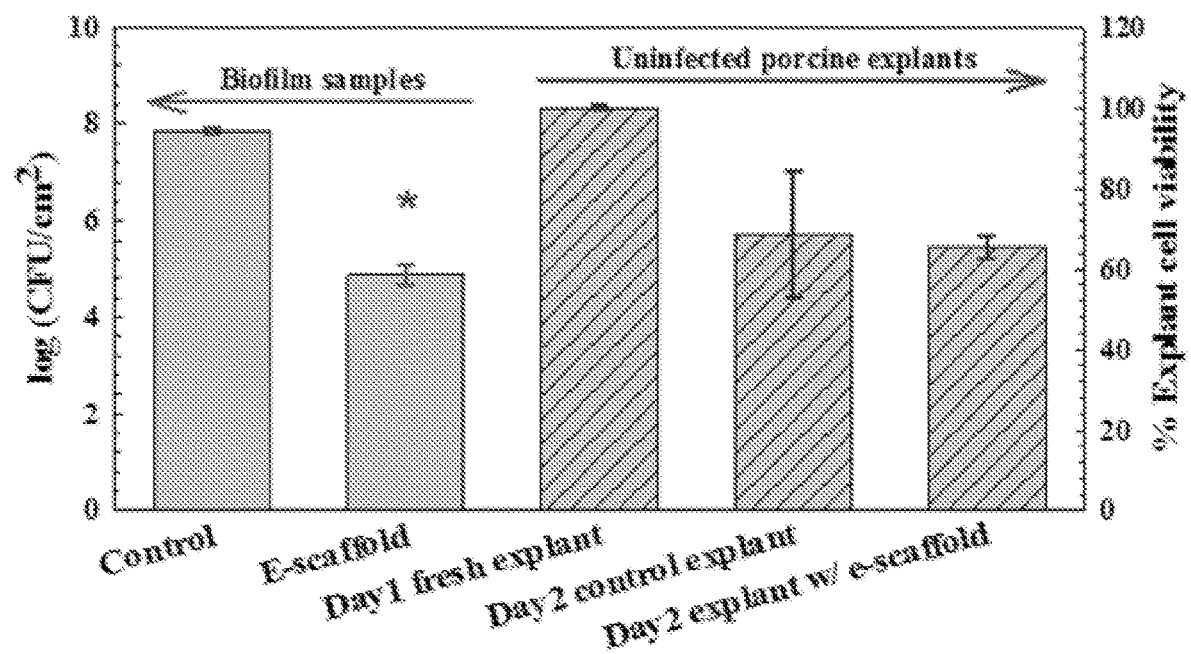
FIG. 8 is another example histogram of a biofilm reduction under various conditions during experiments using the using the experimental setup in FIG. 3 in accordance with embodiments of the disclosed technology. The symbol * denotes a significant difference compared to treatment with an e-scaffold alone (n=3 and P<0.001, one-way ANOVA with Bonferroni post hoc t-test).
Figure 9:
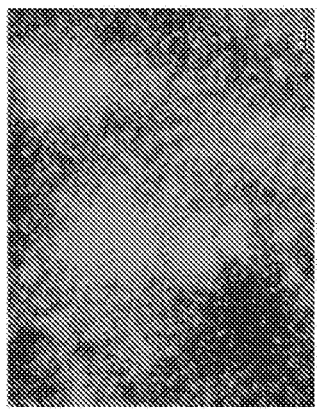
FIGS. 9A-9K are images of a *A. baumannii* biofilm grown for 1 day under various test conditions using an e-scaffold and maltodextrin (MD). Concentrations tested were 36 mg/mL MD (10 mM), 72 mg/mL MD (20 mM), 108 mg/mL MD (30 mM) and 144 mg/mL MD (40 mM).

The efficacy of hydrogen peroxide generated from the e-scaffold was tested against infected porcine explants. A ~3-log reduction in CFU for e-scaffold treated biofilms was observed, as shown in FIG. 8. 95% of the tissue cells in the e-scaffold treated uninfected explants remained viable compared to the untreated control, as measured using a viability stain (n=3, P=0.85). Blinded histological assessments showed that there was no significant damage to the underlying tissue given exposure to the potentiated e-scaffold. The experimental results described above show that the e-scaffold reduced a biofilm community by four orders of magnitude via generation of reactive hydrogen peroxide during experiments without apparent damage to the underlying tissue.

E-Scaffold with Hyperosmotic Agent(S)

As discussed above, electrochemical scaffolds can produce a continuous supply of $H_2O_2$ suitable for damaging or destroying biofilms on wounds of a host without damaging host tissue. However, under certain conditions, with $H_2O_2$ degradation can limit efficacy of such electrochemical scaffolds. The inventors have recognized that the efficiency of H2O2 diffusion into biofilms and bacterial cells can be increased by damaging biofilm structures and/or activating H2O2 membrane transportation channels using hyperosmotic agents. In accordance with several embodiments of the disclosed technology, a combination of an e-scaffold and a hyperosmotic agent (e.g., maltodextrin) can be an effective technique for reducing or even eliminating biofilms. As discussed in more detail below, e-scaffolds are shown to be effective against *Acinetobacter baumannii* and *Staphylococcus aureus* biofilms in the presence of a hyperosmotic agent (e.g., maltodextrin). Even though maltodextrin is used herein as an example of a hyperosmotic agent, in other embodiments, the hyperosmotic agent can include any osmotic compound with generally equivalent osmotic pressure of maltodextrin to decrease water activity in the bacterial cytoplasm. Examples of such hyperosmotic agents can include medical-grade honey, sucrose, mannitol, sorbitol, polyglycerol, glycine, and/or combinations thereof.

In the experiments discussed in more detail below, e-scaffolds of conductive carbon fabric were overlaid onto existing biofilms in media containing various maltodextrin concentrations. *A. baumannii* and *S. aureus* biofilm cell densities were decreased by log (3.92±0.15) (n=3, P<0.001) and log (2.31±0.12) (n=3, P<0.001), respectively, by e-scaffold alone. In contrast, a maximum reduction in *A. baumannii* biofilm cell density of log (4.35±0.16) was achieved in the presence of 10 mM maltodextrin (n=3, P<0.001), and a maximum reduction in *S. aureus* biofilm cell density of log (2.40±0.17) was achieved in the presence of 30 mM maltodextrin (n=3, P<0.001), compared to treatment with e-scaffold alone. Thus, compared to untreated biofilms, e-scaffolds and maltodextrin together achieved log (8.27±0.05) (n=3, P<0.001) and log (4.71±0.12) (n=3, P<0.001) reductions in *A. baumannii* and *S. aureus* biofilm cell densities, respectively. As such, at least for certain applications, H2O2 electrochemically generated from e-scaffolds combined with a hyperosmotic agent such as maltodextrin can be more effective in decreasing viable biofilm cell density than applying the H2O2 alone.

Without being bound by theory, it is believed that H2O2 can destroy bacterial cells by causing irreversible oxidative damage to thiol groups of bacterial proteins and lipids as well as damages to DNA of such bacteria. Nevertheless, it is believed that efficacy of H2O2 is dependent at least in part on how the bacterial population responds to oxidative stress and can differ for Gram-negative and Gram-positive bacteria. The entry of H2O2 into bacterial cells can be limited as a function of lipid composition, diffusion-facilitating channel proteins, or both. Furthermore, the presence of catalase can decompose H2O2, and thus serving as a permeability barrier for the bacterial cells.

Characteristics of a biofilm such as density and reactivity with H2O2 can influence a rate of diffusion of H2O2 into a biofilm. It is believed that when exposed to a negative potential (~−700 mVAg/AgCl), bacterial cells respond by generating osmolytes, including trehalose, betaine, proline and glutamate, that can protect cells from external injuries. These osmolytes likely scavenge e-scaffold-generated H2O2, and thus retard H2O2 entry into bacteria cells and consequently decrease efficiency of e-scaffolds.

Several embodiments of the disclosed technology can facilitate H2O2 entry into bacterial cells by activating bacterial membrane transportation channels in a low osmolarity medium containing a hyperosmotic agent. For example, bacteria can respond to conditions of low osmolarity by increasing the density of membrane porins, especially aquaporin, which in turn can enhance H2O2 entry into cells. A hyperosmotic agent at low osmolarity can thus induce oxidative damage by altering gene expression, including altering catalase expression. A hyperosmotic agent can also enhance H2O2 entry into cells by "stretching" a lipid bilayer of bacteria. However, further increasing the osmolarity of the medium with a hyperosmotic agent can cause blockage of the transportation pathway. In addition, at higher osmolarities, bacteria can synthesize more osmolytes that protect the cells by impeding antimicrobial entry. Therefore, several embodiments of the disclosed technology are directed to techniques for determining optimal ranges of hyperosmotic agent concentrations for obtaining effective H2O2 entry.

As discussed above, an e-scaffold can produce a generally continuous and constant supply of H2O2 (e.g., ~25 μM), which is sufficient to reduce *A. baumannii* populations by log (4±0.28) for both in vitro biofilms and biofilm-infected porcine explants. The inventors have recognized that operations of e-scaffolds in the presence of a hyperosmotic agent such as maltodextrin would be more effective than applying the e-scaffolds alone. Maltodextrin is a product of hydrolyzed starch and is composed of sugars and polysaccharides. Since osmotic responses can differ between Gram-positive and Gram-negative bacteria, optimal concentration ranges of maltodextrin can also vary between different types (e.g., *A. baumannii* and *S. aureus*) biofilms. As described in more detail below, experiments were conducted to treat biofilm samples with an e-scaffold or with a combination of an e-scaffold and maltodextrin. The experiments quantified the changes in biofilm structure and cell viability.

E-Scaffold with Hyperosmotic Agent Experiments

Strains of *Acinetobacter baumannii* and *Staphylococcus aureus* expressing green fluorescent protein were used for the experiments. Cultures were grown in Luria Broth (LB) medium (Sigma-Aldrich, catalog #L3522) supplemented with ampicillin (100 μg/mL; Sigma-Aldrich, catalog #A5354) and tryptic soy broth (TSB) medium (Fisher Scientific, catalog #211825) supplemented with chloramphenicol (10 μg/mL, catalog #C191925G), respectively. All cultures were grown overnight at 37° C. at an agitation speed of 135 rpm on a rotary shaker.

LB medium (5% v/v) with ampicillin (100 µg/mL) was used for *A. baumannii* biofilm culture. TSB medium (10% v/v) with chloramphenicol (10 µg/mL) was used for *S. aureus* biofilm culture. Overnight cultures were adjusted to OD600≈0.5 before use as inocula. Sterile glass bottom petri dishes were inoculated with 2 ml of overnight cultures. After 2 hours of initial attachment, suspended bacteria were removed by washing twice with fresh medium. Biofilms were allowed to develop for 24 hours.

Biofilm Treatment with Maltodextrin and E-Scaffold

Maltodextrin (Sigma Aldrich, catalog #419672) solutions were prepared in the respective growth media. After 24 hours of growth, *A. baumannii* and *S. aureus* biofilms were imaged to collect baseline data. Fresh media (4 ml) with different final concentrations of maltodextrin (0, 5, 10, 20, 30, or 40 mM) were added back to the biofilms. The e-scaffolds were then placed on top of the biofilms.

Cells expressing GFP were imaged using an inverted epifluorescence microscope with a camera mounted thereon. Each biofilm was imaged after 24 hours of growth before any treatment (initial biofilm, t=0 hour) and after 24 hours of treatment. Biofilms were washed twice to remove any planktonic cells and refreshed with medium prior to imaging. The images were evaluated using Image Structure Analyzer ("ISA") software. At least ten discrete images were taken for each time point. Surface coverage was defined as the ratio of the area of biofilm to the total area of the image.

All biofilms exposed to an e-scaffold and/or maltodextrin were collected after 24 hours, and viable cells were enumerated. Biofilms were washed twice with fresh medium to remove loosely attached cells, after which they were recovered from the e-scaffold using sonication and from glass surfaces of the petri dish through resuspension in 5 ml of fresh medium. The suspensions were centrifuged (4,180 g for 10 min), each resulting cell pellet was re-suspended in 1 ml of medium, and serial dilutions were prepared. Colony forming units ("CFU") of viable biofilm cells were quantified using a modified drop-plate method. At least three independent replicates were completed for each set of experimental conditions. Technical replicates were averaged before analysis using one-way ANOVA with a Bonferroni pairwise test to identify differences between treatment groups.

After 24 hours, the untreated and maltodextrin-treated biofilms had similar structures with single and small cell clusters, whereas the initial bright clusters of gfp producing cells were visibly less intense after 24 hours of exposure to the e-scaffold, as shown in FIGS. 9A-9K and FIGS. 11A-11K. When maltodextrin was used in conjunction with an e-scaffold, the bright cell clusters were reduced further. This decrease was particularly evident for e-scaffolds with 10 mM maltodextrin (*A. baumannii*) and e-scaffolds with 30 mM maltodextrin (*S. aureus*).

Figure 10:
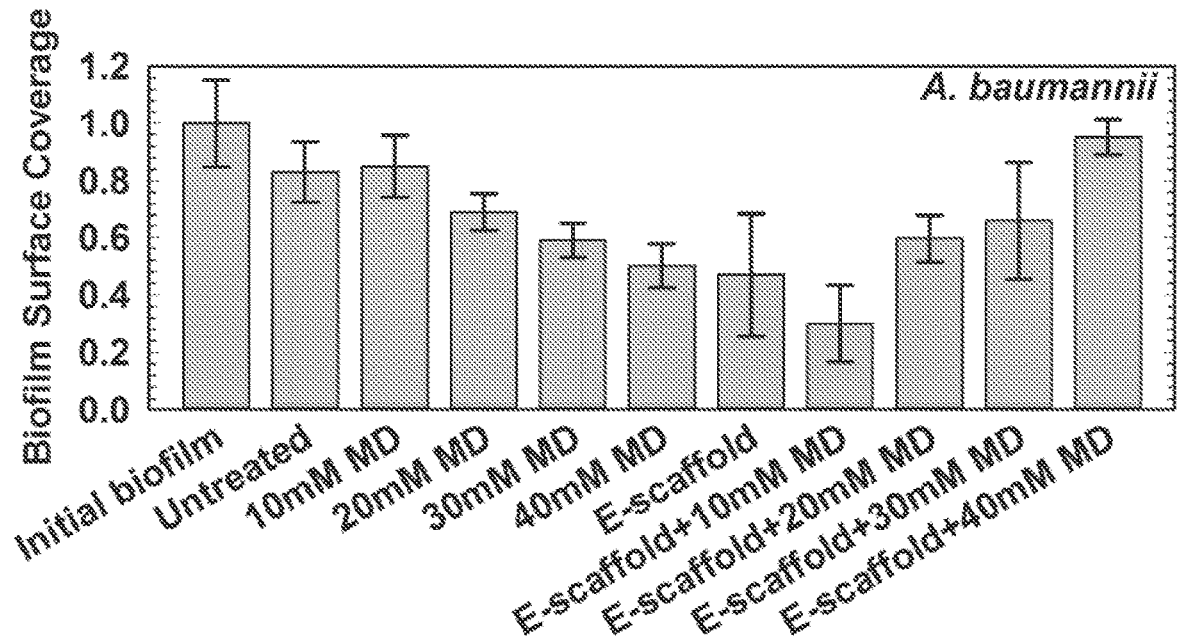
FIG. 10 is a bar graph illustrating a surface coverage for untreated biofilms and biofilms under various testing conditions of maltodextrin (MD) and e-scaffold. Concentrations tested were 36 mg/mL MD (10 mM), 72 mg/mL MD (20 mM), 108 mg/mL MD (30 mM) and 144 mg/mL MD (40 mM).

The average biofilm surface coverage decreased with the combined treatment of an e-scaffold and maltodextrin. As shown in FIG. 10, over the 24 hour treatment period, the untreated *A. baumannii* biofilm decreased ~16.7%. Addition of maltodextrin (10, 20, 30, or 40 mM) resulted in a nearly linear dose-dependent decrease with respect to the initial biofilm surface coverage (r=0.99; 85.21±10.7%, 69.12±6.5%, 58.45±6.0% and 50.0±7.7%, respectively). When *A. baumannii* biofilms were challenged with both an e-scaffold and 10 mM maltodextrin, surface coverage decreased by an additional ~17% compared to the e-scaffold-only treated biofilms (FIG. 10). FIG. 10 also shows that applying a combination of e-scaffold and >20 mM maltodextrin to the biofilms, the biofilm surface coverage increased, as shown in FIG. 10. Combining the e-scaffold with 10 mM maltodextrin decreased biofilm coverage by ~70% of the initial biofilm coverage.

Figure 12:
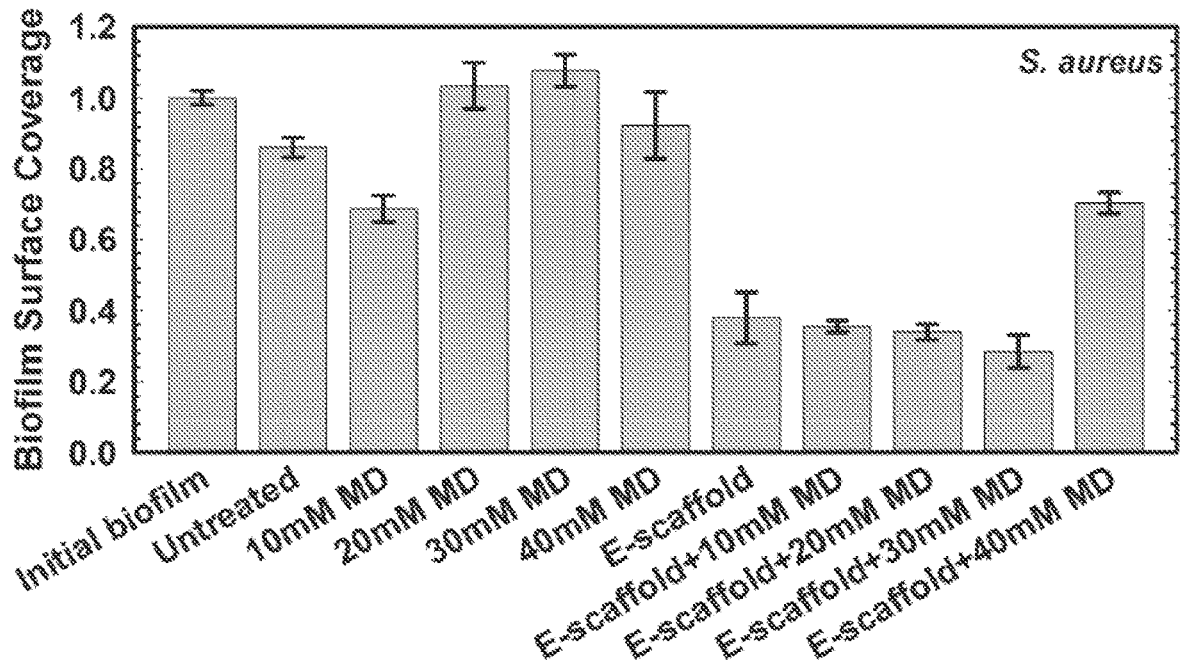
FIG. 12 is a bar graph illustrating a surface coverage for untreated biofilms and biofilms under various testing conditions of maltodextrin (MD) and e-scaffold. Concentrations tested were 36 mg/mL MD (10 mM), 72 mg/mL MD (20 mM), 108 mg/mL MD (30 mM) and 144 mg/mL MD (40 mM).

A similar effect was observed for *S. aureus* biofilms as shown in FIG. 12. The average surface coverage of untreated *S. aureus* biofilms decreased ~14% from that of the initial biofilm (P=0.56). Interestingly, the addition of maltodextrin alone did not produce a linear response with respect to changes in biofilm surface coverage (r=0.54; 70±4.0%, 104±6.43% 108±4.5% and 92.4±9.4%, respectively). When a combination of e-scaffold and maltodextrin (10, 20 and 30 mM) was applied, however, the average surface coverage decreased linearly (r=0.97; 35.6±1.6%, 34.0±2.22% and 28.5±4.7%, respectively). Addition of 40 mM maltodextrin resulted in increased biofilm surface coverage (71.5±2.8%). Thus, the maximum decrease in *S. aureus* biofilm surface coverage (~72% of initial biofilm) was observed with the combination of an e-scaffold and about 30 mM maltodextrin.

Figure 13:
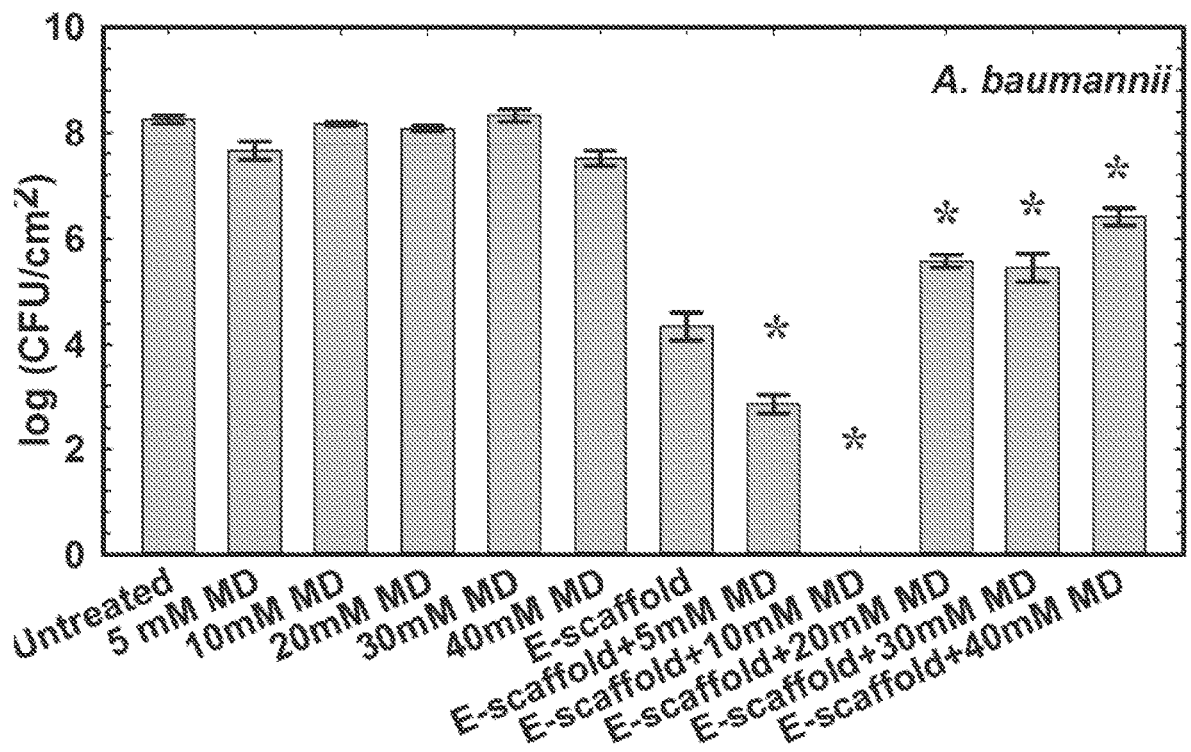
FIG. 13 is a bar graph showing means of log (CFU/cm2) of viable biofilm cells of *A. baumannii* for three tested biological replicates. Error bars represent a standard error of the means calculated from triplicate measurements. The symbol * denotes a significant difference compared to treatment with an e-scaffold alone (n=3 and P<0.001, one-way ANOVA with Bonferroni post hoc t-test). E-scaffolds were polarized at −600 mVAg/AgCl and the average current density was −56 $\mu A/cm^2$.

Treatment with an e-scaffold alone reduced the viable *A. baumannii* biofilm cell density by log (3.92±0.15) compared to that of untreated biofilms as shown in FIG. 13. Addition of maltodextrin (5, 10, 20, 30 and 40 mM) changed the average CFU recovery from *A. baumannii* biofilms compared to e-scaffold treatment alone (one-way ANOVA, P<0.001). This resulted in a "U-shaped" dose response with respect to log-counts of recovered bacteria (2.85±0.17, 0, 5.57±0.12, 5.44±0.27 and 6.41±0.16, respectively). No *A. baumannii* were recovered from biofilms treated with an e-scaffold and 10 mM maltodextrin. Thus, a log (4.35±0.16) reduction of viable biofilm cell density compared to that for an e-scaffold alone indicates that the e-scaffold appeared to be more effective against *A. baumannii* biofilms when used in combination with 10 mM maltodextrin.

Figure 14:
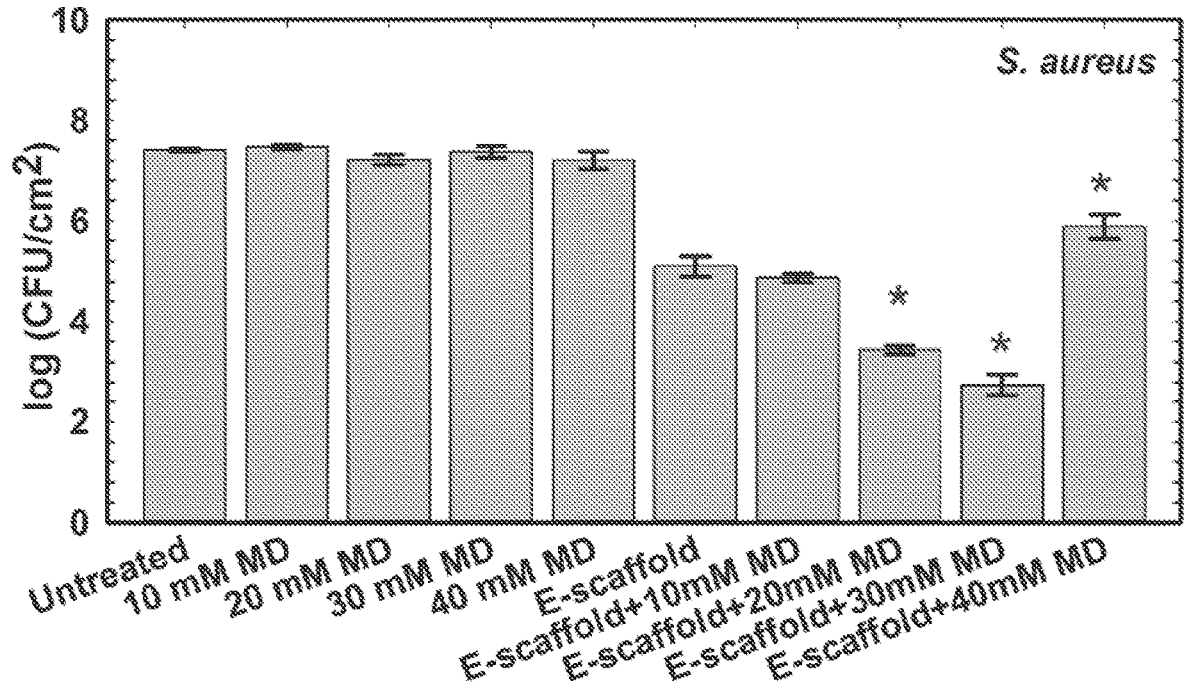
FIG. 14 is a bar graph showing means of log (CFU/cm2) of viable biofilm cells of *S. aureus* for three tested biological replicates. Error bars represent a standard error of the means calculated from triplicate measurements. The symbol * denotes a significant difference compared to treatment with an e-scaffold alone (n=3 and P<0.001, one-way ANOVA with Bonferroni post hoc t-test). E-scaffolds were polarized at −600 mVAg/AgCl and the average current density was −60 $\mu A/cm^2$.

The cell counts for e-scaffold-treated *S. aureus* biofilms decreased by log (2.31±0.12) compared to those for the untreated biofilms as shown in FIG. 14. Addition of 10 or 20 mM maltodextrin in combination with the e-scaffold resulted in a further decrease in log-count to 4.88±0.08 or 3.44±0.08, respectively (FIG. 14). Addition of 30 mM maltodextrin resulted in an additional log (2.40±0.17) reduction in recoverable *S. aureus* compared to treatment with an e-scaffold alone.

Treatments of Persister Cells with E-Scaffold

Biofilms in chronic wounds can contain a "persister" subpopulation that exhibits enhanced multi-drug tolerance and can quickly rebound after treatments. The presence of these "persister cells" can cause failure of antibiotic therapies and incomplete elimination of biofilms. Several embodiments of the disclosed technology are directed to electrochemical processes combined with antibiotics an effective technique for treating biofilm and persister cells. As discussed in more detail below, electrochemical scaffolds can be utilized to electrochemically generate H2O2 for enhancing antibiotic (e.g., tobramycin) susceptibility in biofilms (e.g., *Pseudomonas aeruginosa* PAO1) and for attacking persister cells. Results showed that e-scaffold enhanced tobramycin susceptibility in *P. aeruginosa* PAO1 biofilms reached a susceptibility at 40 µg/ml tobramycin, resulted in generally complete elimination (7.8-log reduction vs. control biofilm cells, P<0.001) of persister cells. The e-scaffold appeared to have eradicated persister cells in biofilms, generally leaving no viable cells (5-log reduction vs. control persister cells, P<0.001). The e-scaffold induced intracellular formation of hydroxyl free radicals were observed. Such improved membrane permeability in e-scaffold treated biofilm cells is believed to have enhanced antibiotic susceptibility, resulted in general eradication of the persister cells.

An e-scaffold can generate H2O2 with applied electrical power. The generated H2O2 is believed to enter bacterial periplasm through porins to induce intracellular production of highly reactive hydroxyl free radicals (OH•) that can degrade membrane lipids, proteins, and DNAs. H2O2 can also eliminate some of the persister cells in biofilms, facilitate disruption of biofilm architecture, and mediate generation of metabolically active dispersal cells in a range of bacterial biofilms. Such metabolic activity in surviving dispersal cells and OH• production can induce bacterial sensitivity to antibiotic treatments. Therefore, e-scaffold generated H2O2 can promote intracellular OH• production that in turn can improve antibiotic sensitivity in biofilms and persister cells.

In accordance with several embodiments of the disclosed technology, P. aeruginosa PAO1 biofilms have been treated with an aminoglycoside antibiotic (tobramycin) in combination with an e-scaffold configured to generate H2O2. P. aeruginosa PAO1 is believed to be resistant to tobramycin by producing periplasmic glucans, mutations of ribosome-binding sites, or increased efflux pump action inhibiting cellular uptake. Furthermore, P. aeruginosa PAO1 persister cells can be less sensitive to tobramycin.

As described in more detail below, persister cells from P. aeruginosa PAO1 biofilms were isolated after being treated with ciprofloxacin. Tobramycin susceptibility of P. aeruginosa PAO1 biofilms treated with an e-scaffold was then compared with the tobramycin susceptibility of such persister cells to evaluate the efficacy of the e-scaffold against persister cells and to determine whether e scaffold treatment would increase intracellular production of OH• radicals and increase membrane permeability in the bacterial cells. In addition, changes in bacterial cell morphology after e-scaffold treatment was observed using scanning electron microscopy ("SEM").

E-Scaffold with Antibiotics Experiments

For the following experiments, 20 g/L (1×) Luria broth (LB) medium (Sigma-Aldrich, catalog #L3522) was used to grow P. aeruginosa PAO1 cultures overnight, and 1 g/L (0.05×) LB was used as the growth medium for biofilms. Tobramycin (Sigma Aldrich, catalog #T4014) and ciprofloxacin (Sigma Aldrich, catalog #17850) solutions were diluted in 1 g/L (0.05×) LB for antibiotic susceptibility experiments and persister cell isolation, respectively. Minimum inhibitory concentrations (MICs) were determined for both antibiotics following the Clinical and Laboratory Standards Institute (CLSI) protocol. Other compounds used include 3'-p-hydroxyphenyl fluorescein dye (Invitrogen, catalog #H36004), propidium iodide (Invitrogen, catalog #L-7012), thiourea (AK Scientific, Inc., catalog #S726), and H2O2 (VWR, Catalog #RC3819-16).

Frozen stocks of P. aeruginosa PAO1 were cultured overnight in LB at 37° C. on a rotating table. For biofilm experiments, overnight culture was adjusted to OD600≈0.5 in LB and used as an inoculum. 2 ml of culture was used to inoculate sterile glass bottom petri dishes and allowed to form biofilms for 24 hours. Such one day-old biofilms were treated with e-scaffolds for 24 hours. Untreated and e-scaffold treated biofilm cells were then washed twice to remove loosely attached cells. Remaining cells were recovered for antibiotic susceptibility testing.

To identify and isolate P. aeruginosa PAO1 persister cells, planktonic culture was grown to the stationary phase and the dose-dependent killing curve for ciprofloxacin (0-200 μg/ml) was investigated. A plateau of the surviving subpopulation was observed for ciprofloxacin concentrations above 50 μg/ml (200× of MIC), and identified as persister cells. Assessments were then performed on biofilms regrown from cells recovered after no treatment ("untreated biofilms"), cells recovered after e-scaffold treatment ("e-scaffold treated biofilm"), and "persister cells" that were isolated from biofilms treated with 200 μg/ml ciprofloxacin for 3.5 hours. The treated samples were washed with 0.9% NaCl and suspended in LB to isolate persister cells from ciprofloxacin-treated biofilms for subsequent experiments as described in more detail below.

Figure 15A:
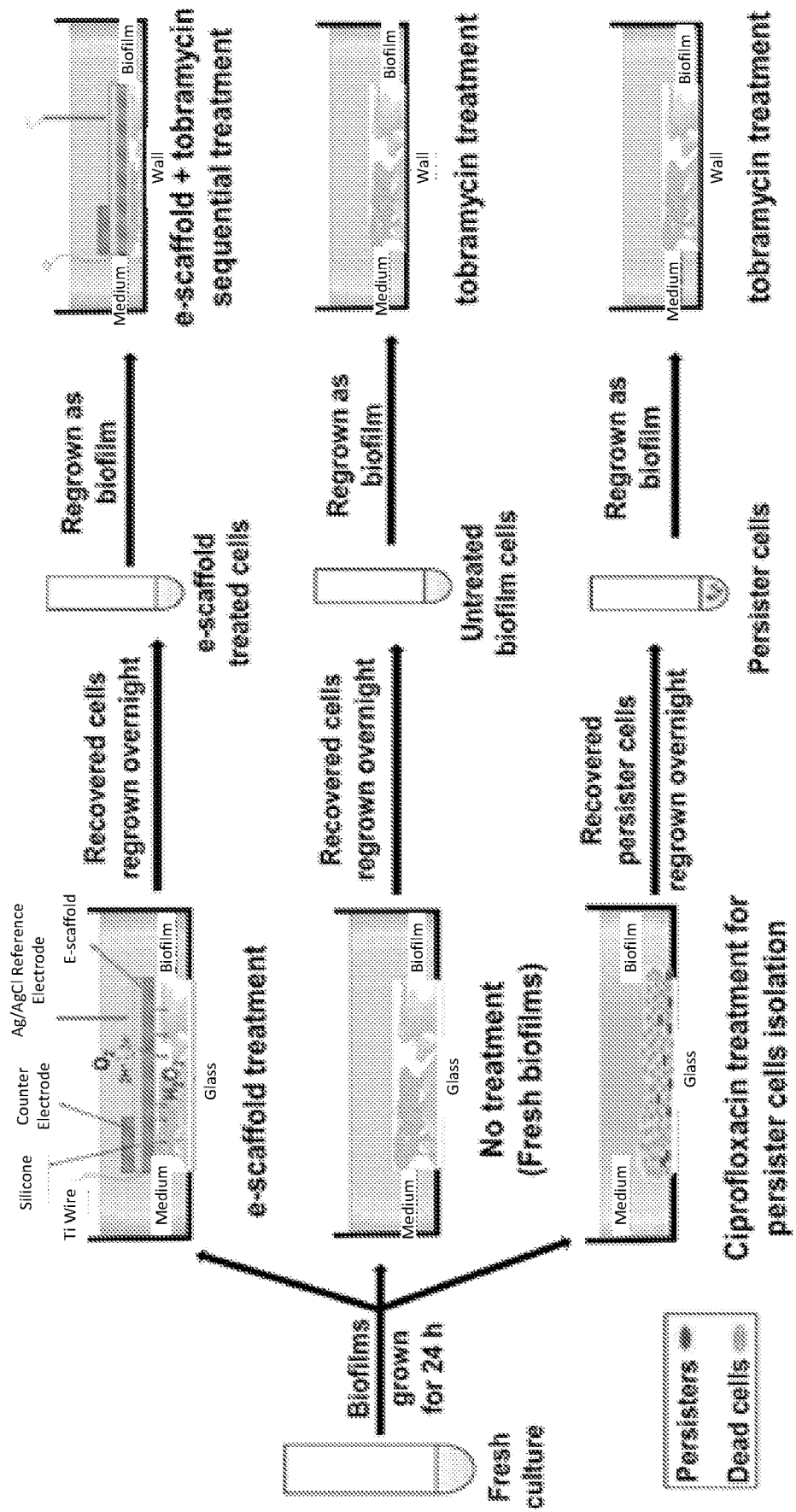
FIG. 15A is a schematic diagram showing operations of recovering biofilm cells treated with e-scaffold and tobramycin in accordance with embodiments of the disclosed technology.

As shown in FIG. 15A, P. aeruginosa PAO1 biofilms were exposed to e-scaffold treatment for 24 hours. Biofilms were washed with LB (0.05×) and an e-scaffold was overlaid onto the biofilms followed by 4 ml of fresh medium. A standard Ag/AgCl (saturated KCl) reference electrode was introduced to apply a generally constant potential (−600 mVAg/AgCl) to an e-scaffold. After treatment, the viable cell counts were determined using a modified drop-plate cell counting method. Loosely attached cells were removed by carefully washing the biofilms with 0.9% NaCl before being re-suspended in 5 ml of 0.9% NaCl and vortexed for 30 seconds. The suspensions were centrifuged (4,180×g for 10 min), and the resulting cell pellet was re-suspended in 1 ml of 0.9% NaCl. Aliquots (250 μL) were then serially diluted, and 10 μL of each dilution was plated onto LB agar. Plates were incubated for 24 hours (37° C.), and colony-forming units (CFUs) were enumerated.

To determine whether e-scaffold treatment altered susceptibility to antibiotics, biofilm treatments were combined with tobramycin. As shown in FIG. 15A, recovered biofilm cells were harvested and adjusted to OD600≈0.5 in LB medium (0.05×). A 1 ml cell suspension was used to inoculate a 24-well plate, on which biofilms were allowed to form. Biofilms were treated with an e-scaffold for 2 hours. Each well was then washed and challenged with 1 ml of one of the test concentrations (5, 10, 20 and 40 μg/ml) of tobramycin for 6 hours. After treatment, the cells were washed and re-suspended in 0.9% NaCl and processed to enumerate CFU. Cell counts were compared for e-scaffold and other treated and untreated biofilms.

Figure 15B:
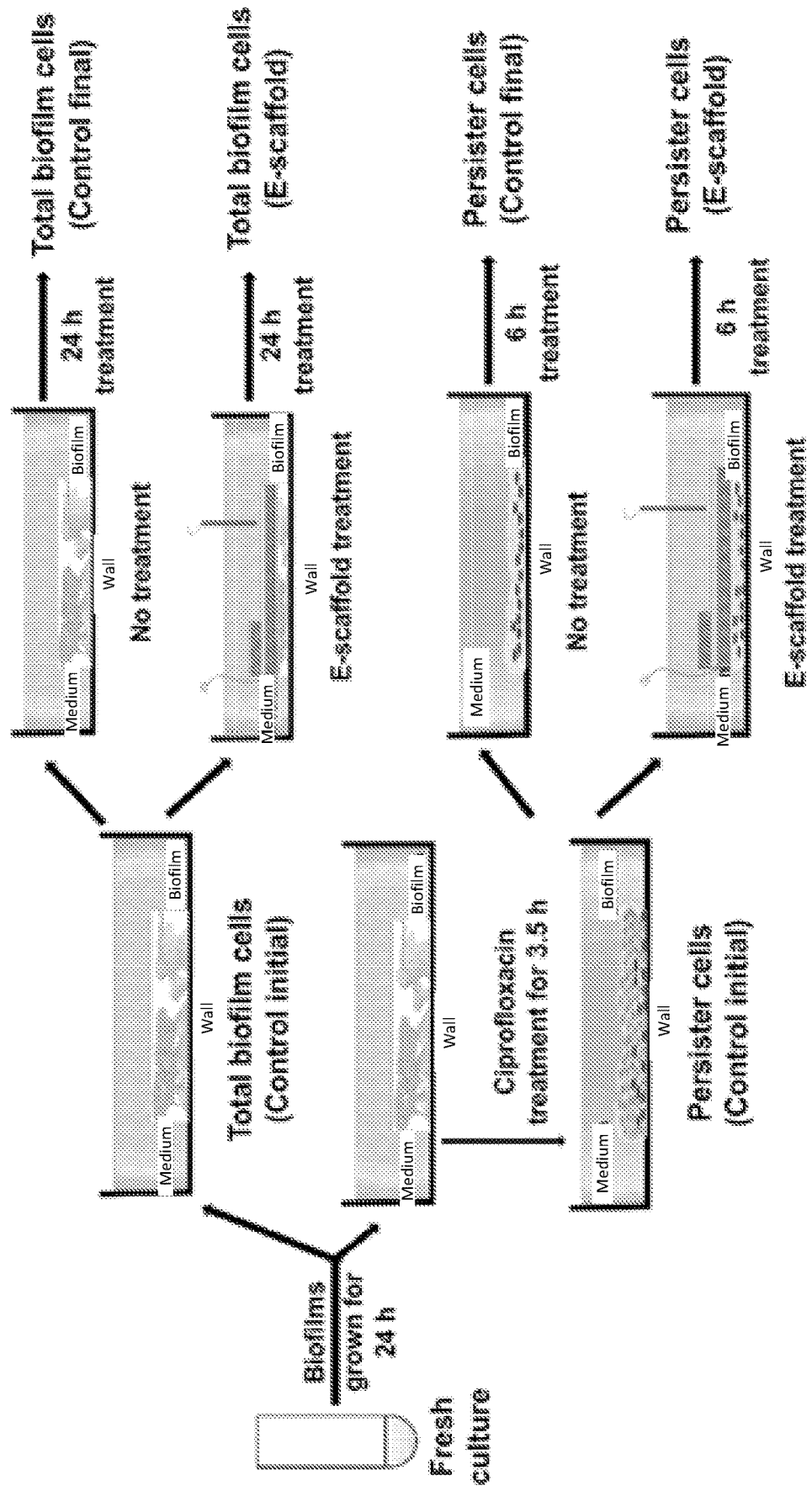
FIG. 15B is a schematic diagram showing operations of treating biofilms and persister cells with e-scaffold in accordance with embodiments of the disclosed technology.

As shown in FIG. 15B, biofilms were grown for 24 hours in 6-well plates and treated with 200 μg/ml ciprofloxacin for 3.5 hours to isolate persister cells from ciprofloxacin-treated biofilms. The total number of viable cells was determined for ciprofloxacin-treated and untreated biofilms using the modified drop-plate cell counting method. Remaining persister cells were then exposed to either 200 μg/ml ciprofloxacin or e-scaffold treatment for 6 hours. Final CFU values were then determined.

Intracellular hydroxyl free radical (OH•) formation was detected using 5 μM of a fluorescent reporter dye, 3'-(p-hydroxyphenyl fluorescein) (HPF). E-scaffold treated, exogenous H2O2-treated, and untreated biofilm cells were vortexed in 500 μL of LB in a micro-centrifuge tube for 30 seconds. The samples were centrifuged (10,000×g for 10 min), and then the medium was replaced with a final concentration of 5 μM HPF prepared in 500 μL of 0.1 M PBS. After staining in the dark at room temperature for 15 minutes, samples were centrifuged at 10,000×g for 10 min. Supernatant was removed, and cells were rinsed and re-suspended with PBS. An aliquot (100 μL) was added to each well in a 96-well plate, and fluorescence intensity was quantified using a microplate reader with excitation at 490 and emission at 515 nm. For the OH• formation assays, fluorescence was estimated as ((Fluorescence with dye– Fluorescence without dye)/(Fluorescence without dye))*(100).

Changes in bacterial membrane permeability were evaluated using propidium iodide (PI) staining. PI is a membrane-impermeable dye and can only enter a bacterial cell if the outer membrane is damaged. Thus, an increase in PI intensity corresponds generally to increased membrane permeability. E-scaffold treated and untreated biofilm cells were stained with PI for 15 minutes in the dark, then washed twice with 0.9% NaCl to remove any unbound dye. Cells were then re-suspended in 0.9% NaCl, and 100 µL of each suspension was transferred in triplicate into wells of a 96-well plate. Fluorescence intensity was quantified (excitation 535 nm, emission 517 nm). Fluorescence was determined as a percentage change compared to untreated sample as ((Fluorescence with dye– Fluorescence without dye)/(Fluorescence without dye))*(100).

For SEM imaging, biofilms were grown for 24 hours on UV-sterilized, 0.22 µm type GV membrane filters placed in sterile 6-well plates. Exogenous $H_2O_2$ was added continuously at an average 0.008 mmol/h for 24 hours to mimic the e-scaffold generated $H_2O_2$ treatment. After treatment for 24 hours, both e-scaffolds and membrane filters with biofilms were aseptically collected from the untreated, e-scaffold treated, and exogenous $H_2O_2$ treated wells. The membrane filters and e-scaffolds were fixed overnight with 2.5% glutaraldehyde and 2% paraformaldehyde in 0.1 M phosphate buffer, followed by rinsing with 0.1 M phosphate buffer. The membranes and e-scaffolds were then dehydrated gradually by being washed sequentially with 10%, 30%, 50%, 70%, and 95% alcohol (10 min each) and 100% alcohol (3×10 min each). Samples were then sputter-coated with gold prior to field emission in-lens scanning electron microscopy imaging.

Figure 16:
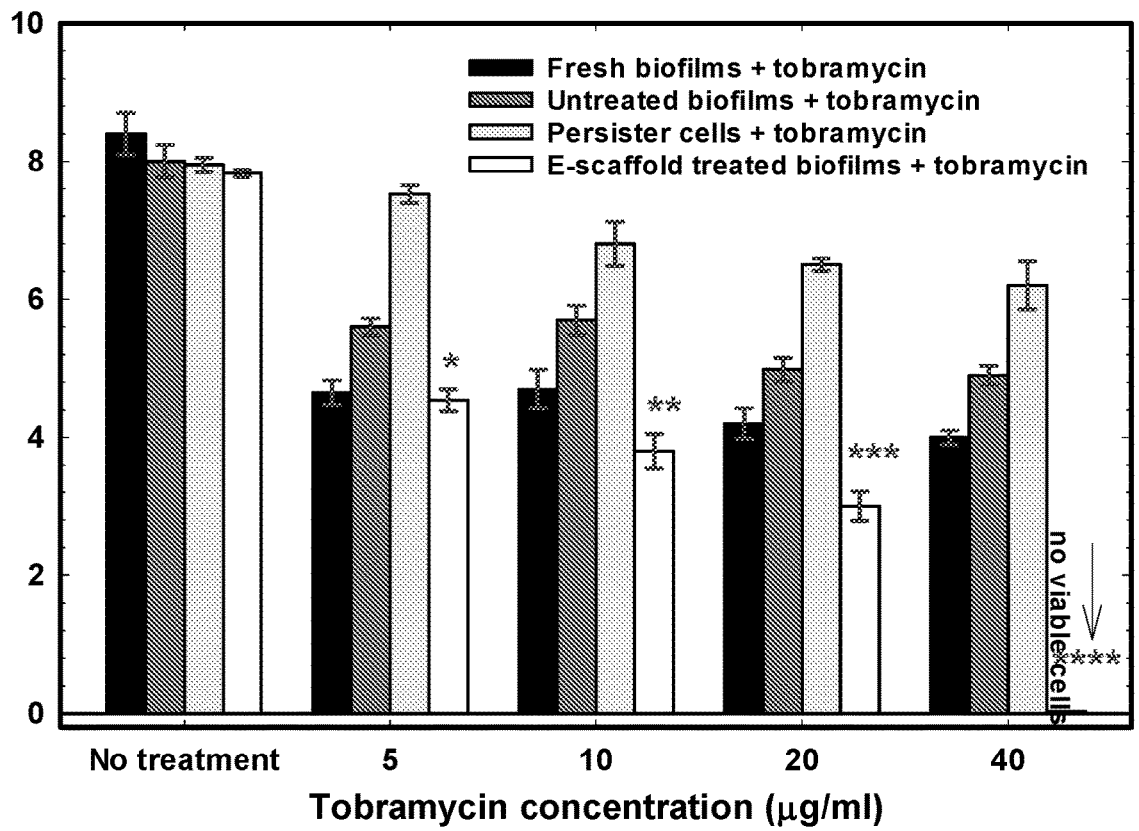
FIG. 16 is a bar graph showing means of logarithms of colony-forming units of viable *P. aeruginosa* PAO1 biofilm cells in accordance with embodiments of the disclosed technology. The symbols *, , *, and **** represent significant differences in tobramycin susceptibility between e-scaffold treated biofilms with tobramycin and untreated biofilm with tobramycin (n=3, *, P=0.002; , *, **** P<0.001; paired t-test).

When biofilm treatments were combined with different concentrations of tobramycin, the surviving cells responded differently. As shown in FIG. 16, the tobramycin susceptibility of *P. aeruginosa* PAO1 biofilms regrown from fresh culture, untreated biofilm cells, and persister cells isolated from biofilms appeared to follow a dose response at tested concentrations between 0 and 40 µg/ml. The biofilms regrown from persister cells showed a higher tolerance to tobramycin, with only a (1.2±0.16)-log reduction in viable cells for 10 µg/ml tobramycin and no further significant decrease at higher concentrations.

The persister cells had the same MIC as the fresh culture; survived antibiotic treatment, regrew and become more tolerant to tobramycin. Interestingly, tobramycin tolerance was observed in biofilms regrown from untreated biofilm cells and persister cells isolated from biofilms. In contrast, no tolerance to tobramycin was identified for biofilms regrown from e-scaffold treated cells when different concentrations of tobramycin were combined with e-scaffold treatment, as shown in FIG. 16. A linear dose response was observed for a log reduction of e-scaffold treated biofilm cells that received tobramycin, leading to a virtually complete eradication at 40 µg/ml tobramycin. This concentration (20× of MIC) is still considerably lower than what is typically required for *P. aeruginosa* PAO1 biofilm treatment with tobramycin (e.g., >500× of MIC). Overall, a significant increase in tobramycin susceptibility was attained for e-scaffold treated biofilms compared to biofilms that were not treated with an e-scaffold ($P<0.05$, paired t-tests). Among the tested tobramycin concentrations, a maximum tobramycin susceptibility at 40 µg/ml in e-scaffold treated biofilms was observed.

Figure 17:
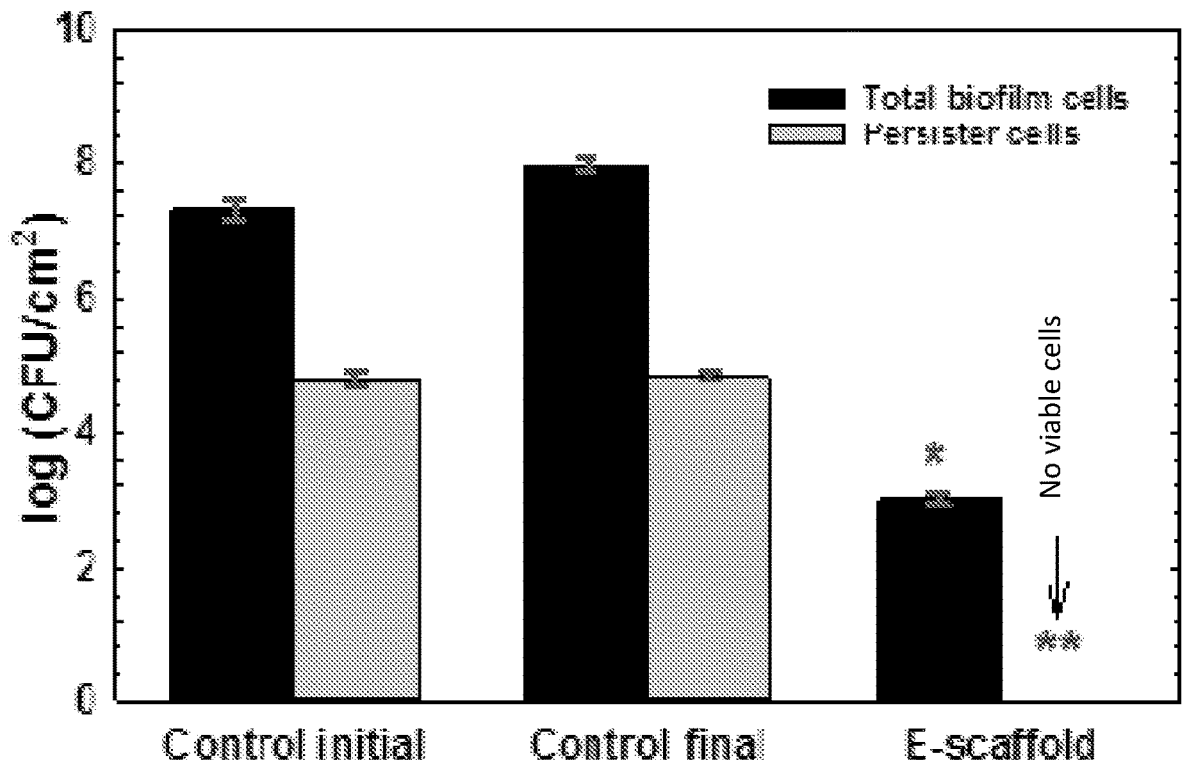
FIG. 17 is a bar graph showing means of logarithms of colony-forming units of viable *P. aeruginosa* PAO1 biofilm cells treated with an e-scaffold in accordance with embodiments of the disclosed technology. The symbol * denotes a significant difference compared to total biofilm cells (n=3, P=0.045, one-way ANOVA); and ** denotes a significant difference compared to control initial persister cells (n=3, P<0.001, one-way ANOVA).

FIG. 17 shows example effects of e-scaffold generated $H_2O_2$ on *P. aeruginosa* PAO1 persister cells isolated from ciprofloxacin-treated biofilms. As shown in FIG. 17, about 0.31% of total biofilm cells belonged to the persister population. Within 6 hours of these persister cells being treated with an e-scaffold, no viable persister cells were apparent, which corresponds to a 5-log reduction in persistence compared to the control initial persister cells ($P<0.001$, one-way ANOVA followed by Bonferroni test). In contrast, final population of persister cells did not change within the additional 6 hours of ciprofloxacin treatment. The e-scaffold was also found to be effective against total biofilm cells, with a (4.95±0.20)-log reduction in viable cells within 24 hours of treatment compared to the control final biofilm cells. These results suggest that the e-scaffold is effective against both regular biofilm cells in active states and persister cells in inactive metabolic states.

Figure 18A:
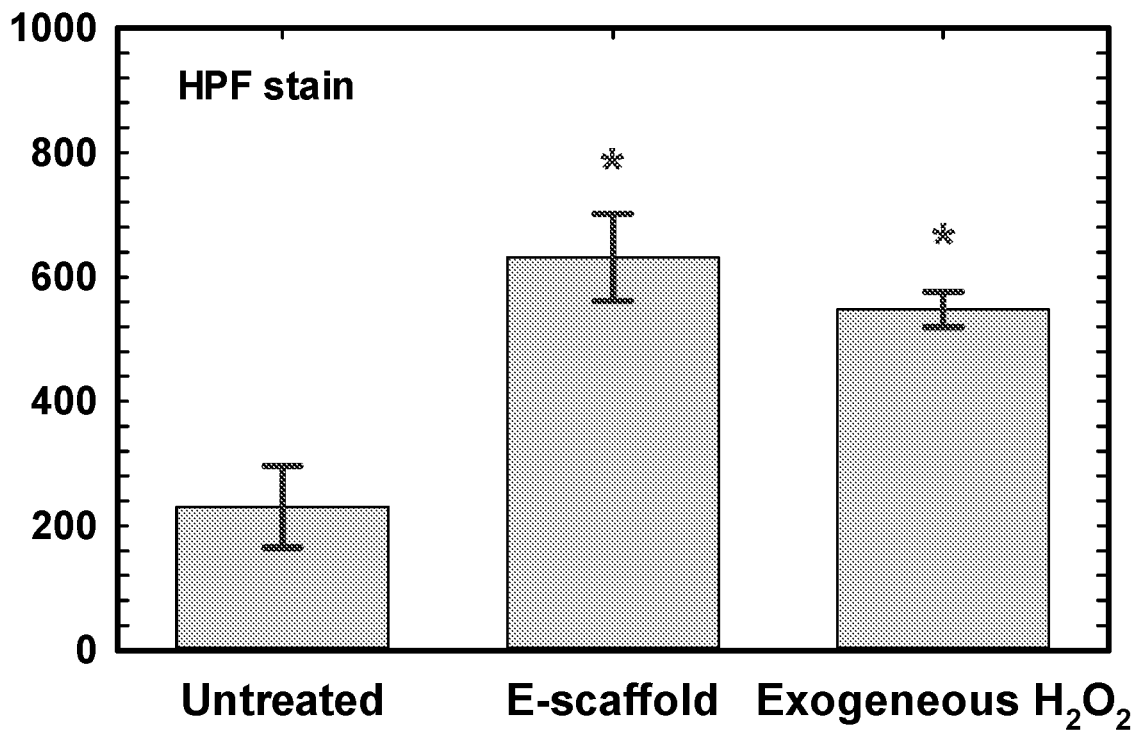
FIG. 18A is a bar graph showing fluorescence of HPF-stained e-scaffold treated and exogenous H2O2 treated *P. aeruginosa* PAO1 biofilm cells in accordance with embodiments of the disclosed technology.
Figure 18B:
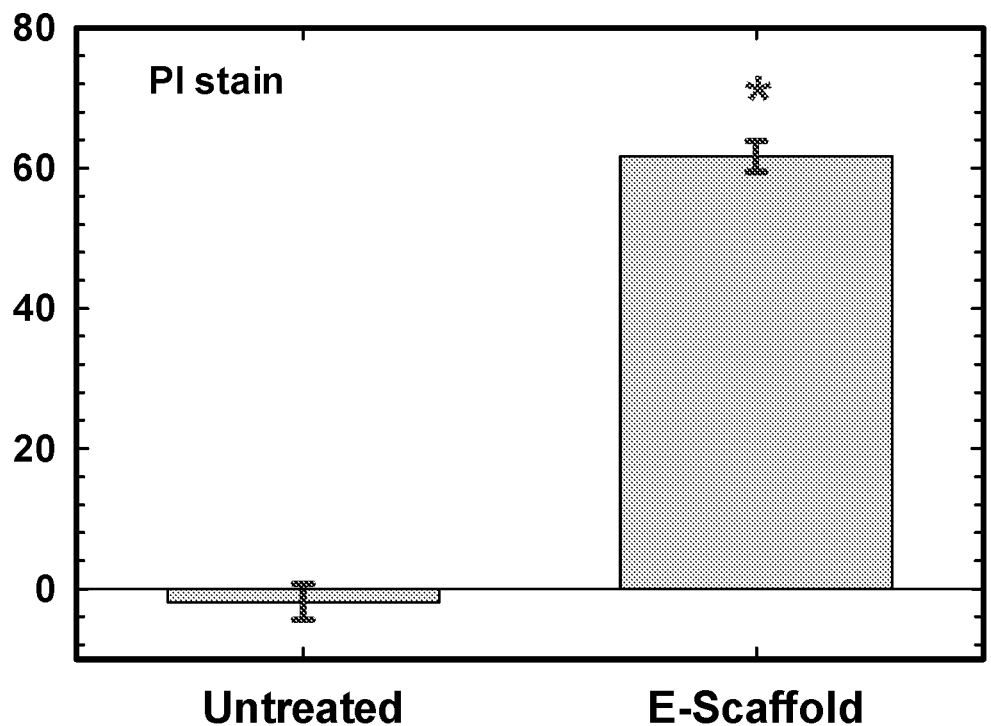
FIG. 18B is a bar graph showing fluorescence of propidium iodide (PI)-stained e-scaffold treated and exogenous H2O2 treated *P. aeruginosa* PAO1 biofilm cells in accordance with embodiments of the disclosed technology.

As shown in FIG. 18A, increased fluorescence was observed for both e-scaffold treated and exogenous $H_2O_2$ treated biofilm cells, indicating enhanced OH• formation after e-scaffold generated $H_2O_2$ treatment. Furthermore, as shown in FIG. 18B, an increase in the PI fluorescence of e-scaffold treated cells was observed compared to untreated biofilm cells. Such results indicate that PI permeability increased in e-scaffold treated cells, indicating that membrane integrity of the cells was compromised by OH•. Additionally, as shown in FIG. 19A-19C, membrane-compromised cells similar to those in exogenous $H_2O_2$ treated samples were observed in e-scaffold treated samples in SEM images. Untreated biofilm cells showed intact cell walls and membranes.

Without being bound by theory, it is believed that biofilm removal using e-scaffolds is electrochemical generation of $H_2O_2$, which is a potential biocide and an oxidizing agent. It is believed that $H_2O_2$ can mediate dispersal in biofilms, disrupts various bacterial processes and cellular networks, and disrupts the cell envelope through intracellular production of ROS such as OH• in Gram-negative bacteria. Experimental results suggested that e-scaffold generated $H_2O_2$ increased intracellular OH• formation in Gram-negative *P. aeruginosa* PAO1 biofilm cells. Furthermore, in membrane permeability assays and SEM image analysis, increased permeability with moderate membrane damage in cells after e-scaffold treatment was observed. Thus, it is believed that when e-scaffold generated $H_2O_2$ enters a bacterial cell, the $H_2O_2$ induces intracellular ROS production such as OH•, which can increase the permeability of bacterial membranes, which can facilitate increased antibiotic penetration.

Figure 20:
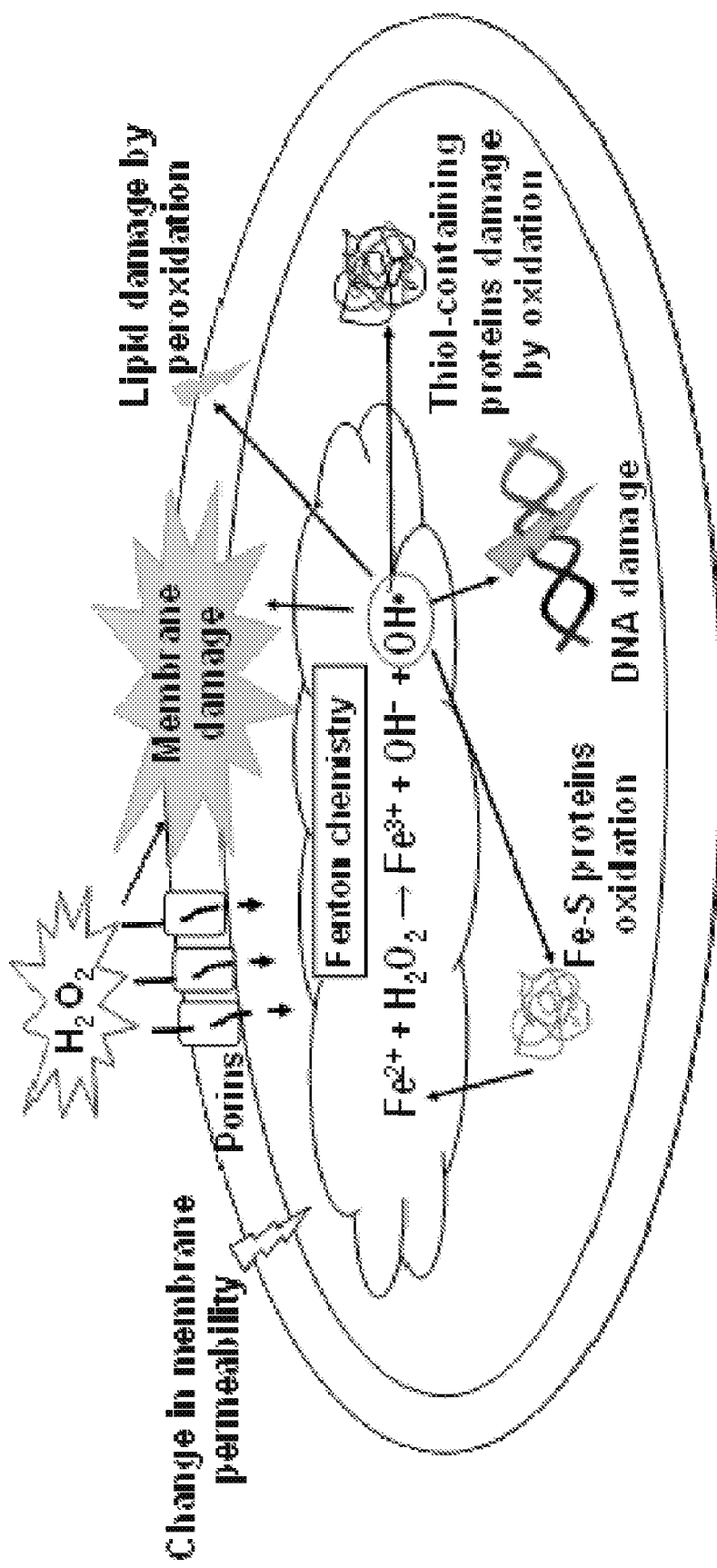
FIG. 20 is a schematic diagram illustrating one possible mechanism via which e-scaffold generated H2O2 can enhance antibiotic susceptibility in accordance with embodiments of the disclosed technology.

Increase in permeability of outer membrane of Gram-negative bacteria via e-scaffolds can be used for enhancing susceptibility to a range of antibiotics. The increased intracellular OH• formation can enhance antibiotic susceptibility in bacteria. As indicated in FIG. 20, OH• formation can occur through a Fenton reaction in which $Fe^{2+}$ plays a role. As shown in FIG. 20, $H_2O_2$ generated extracellularly by e-scaffold can diffuse through the bacterial cell envelope and reacts with intracellular $Fe^{2+}$, forming radicals that oxidize lipids, proteins and DNA, to prompt cell death. Through membrane damage or changing membrane permeability antibiotic penetration into the bacterial cell is increased, which in turn enhances the antibiotic susceptibility of the cells.

Hypochlorous Acid Generation Using E-Scaffolds

Even though various embodiments of the disclosed technology are directed to using hydrogen peroxide produced by e-scaffolds to treat biofilms, in other embodiments, embodiments of the e-scaffolds can also be used to produce other suitable biocides. In one example, the treatment system 100 in FIG. 1 can be modified to produce hypochlorous acid to treat biofilms by pre-loaded or combined during treatment with sodium chloride (NaCl), potassium chloride (KCl), or other soluble chlorides. Similar to H2O2, HOCl is unstable in a solution and can shift to either chlorine specie or sodium hypochlorite (NaOCl) depending on a pH of the solution. Solutions of HOCl also degrade rapidly.

During operation, it is believed that the applied electrical potential via the first and second electrodes 122 and 124 can generate HOCl at a desired concentration by electrochemically converting chlorine and water as follows:

$$H_2O + Cl^- \rightleftarrows HOCl + H^+$$

Figure 21A:
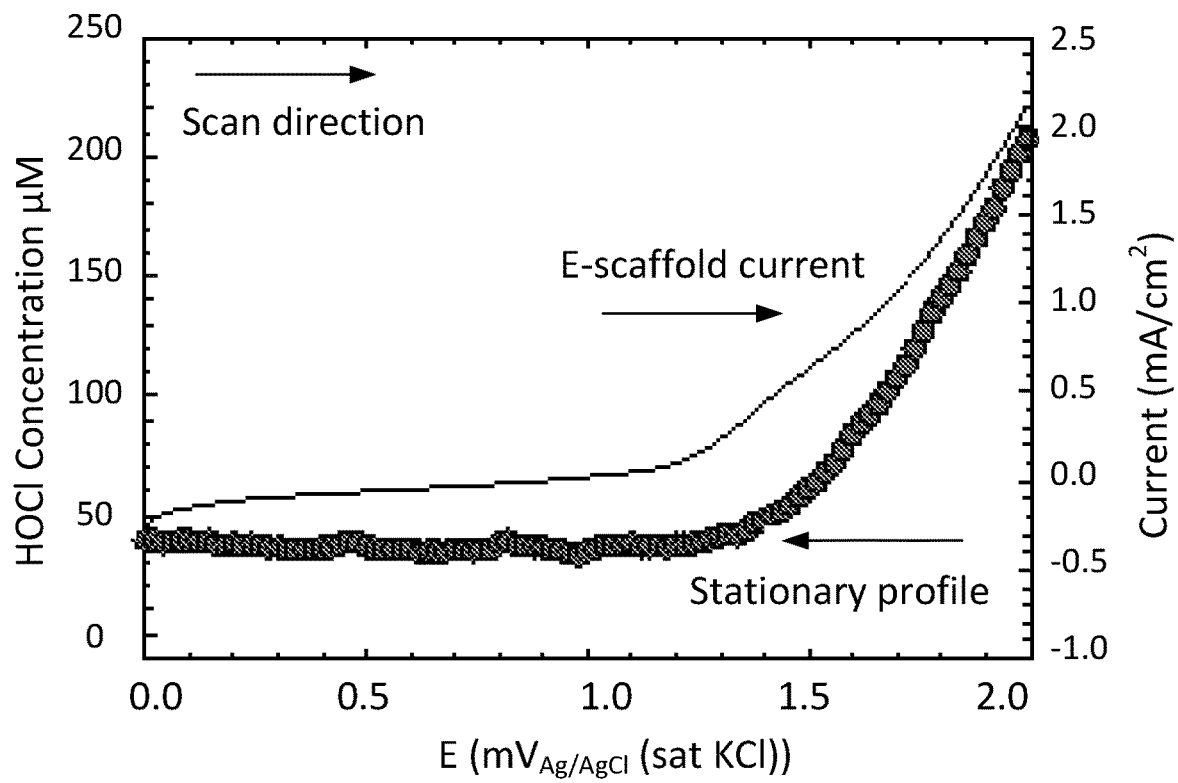
FIG. 21A is a plot of hypochlorous acid (HOCl) concentration in μM at about 50 μM from the polarized surface of an example e-scaffold at potentials ranging from about 0 VAg/AgCl to about 2 VAg/AgCl.
Figure 21B:
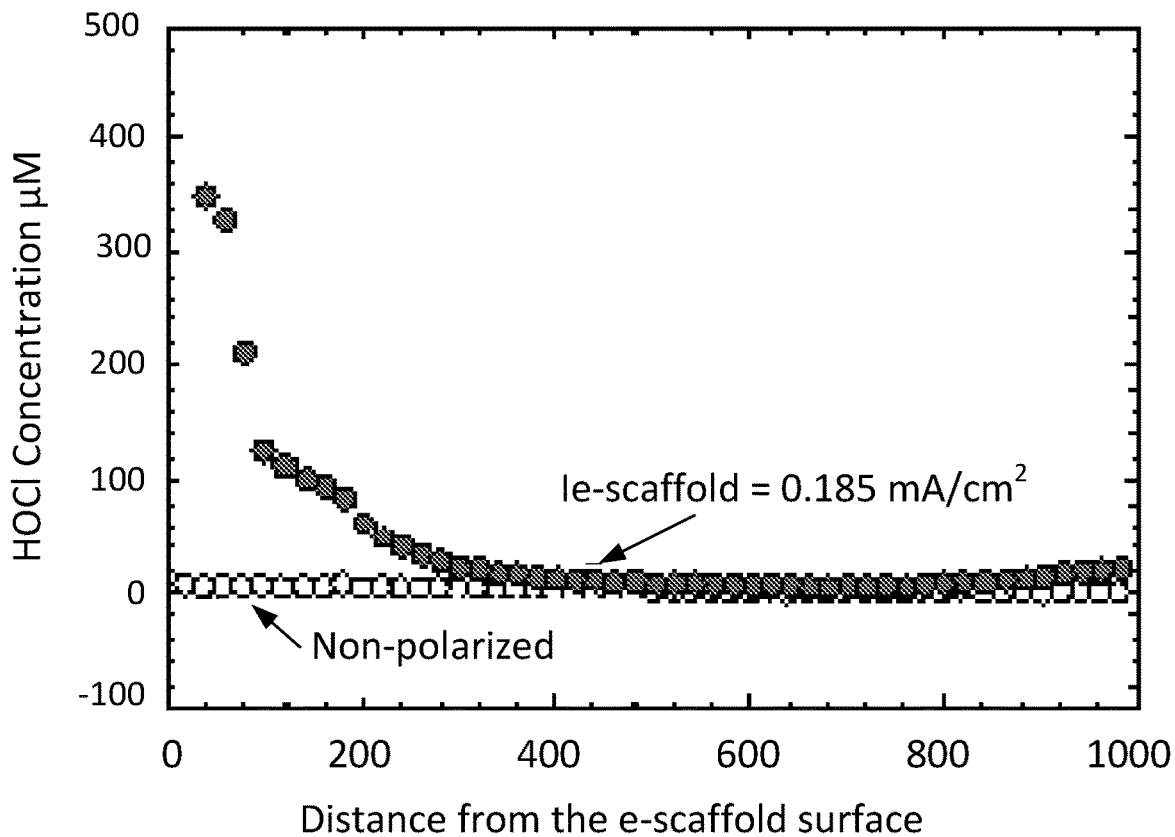
FIG. 21B is a plot of hypochlorous acid (HOCl) concentration depth profiles on both non-polarized and polarized e-scaffold at 1.5 VAg/AgCl. The x-axis depicts the distance of the microelectrode from a surface of the example e-scaffold to the bulk with a distance value of zero being the surface of the e-scaffold. The unit of HOCl is μM.

Experiments were conducted using a carbon fabric to construct the first and second materials 112 and 114 which was submerged in a 0.9% sodium chloride (NaCl) solution. Microelectrode was used to detect the production of HOCl near the e-scaffold surface. In vitro experiments demonstrated that about 50 μM of HOCl was generated near the e-scaffold surface at a potential of about 1.5 VAg/AgCl. As shown in FIGS. 21A and 21B, at about 1.2 VAg/AgCl and beyond, water electrolyzed and Cl– oxidized to HOCl.

Figure 22:
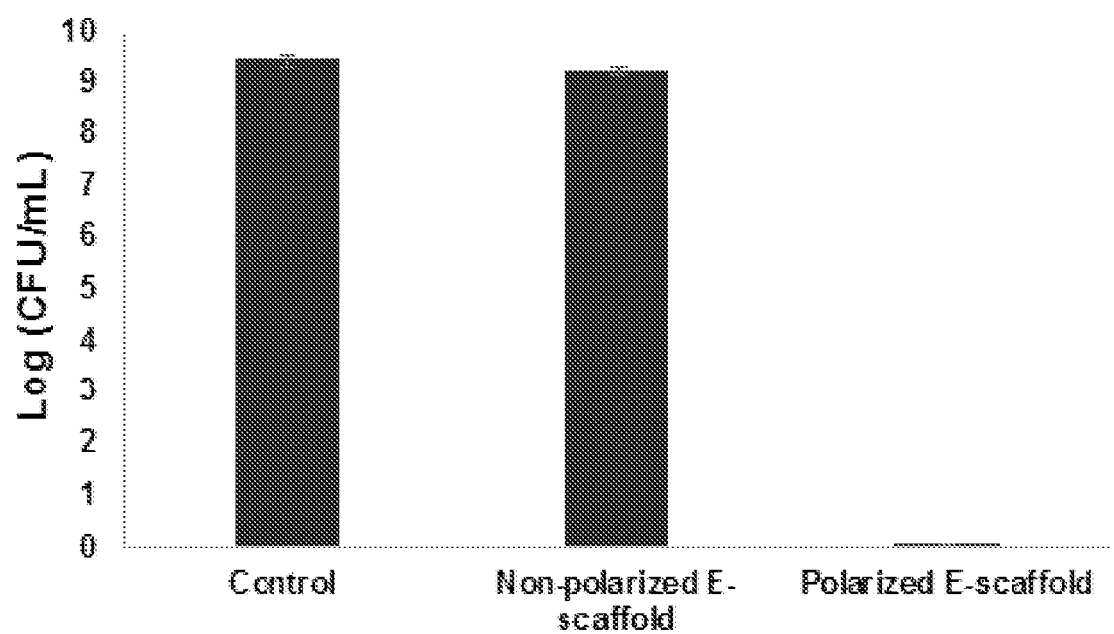
FIG. 22 is a bar graph showing CFU count of viable cells from *S. aureus* biofilms with and without treatment of an e-scaffold polarized at 1.5 VAg/AgCl from conducted experiments.

To test the efficacy of electrochemically generated HOCl, an e-scaffold was overlaid on *Staphylococcus aureus* biofilms. As shown in FIG. 22, after about 12 hours of exposure, HOCl generated by an example e-scaffold completely eradicated *S. aureus* biofilms.

From the foregoing, it will be appreciated that specific embodiments of the disclosure have been described herein for purposes of illustration, but that various modifications may be made without deviating from the disclosure. In addition, many of the elements of one embodiment may be combined with other embodiments in addition to or in lieu of the elements of the other embodiments. Accordingly, the technology is not limited except as by the appended claims.

We claim:

1. A dressing for reducing or preventing bacterial infection to an open wound, the dressing comprising:
a first material configured to contact a surface of the open wound;
a second material spaced apart from the first material;
first and second electrodes electrically coupled to the first and second materials, respectively;
a power source having output electrically coupled to the first electrode at a first polarity and to the second electrode at a second polarity opposite the first polarity, wherein the power source includes a voltage controller that is calibrated to bias the first and second materials via the first and second electrodes to a voltage differential corresponding to a concentration of hydrogen peroxide ($H_2O_2$) via an electrochemical reaction between oxygen and water at the surface of the wound as follows: $O_2 + 2H^+ + 2e^- \leftrightarrows H_2O_2$;
a voltage sensor operatively coupled to the voltage controller, the voltage sensor being configured to detect the voltage differential between the first and second materials;
wherein the voltage controller is configured to maintain the voltage differential at approximately a setpoint based on the detected voltage differential between the first and second materials;
a hydrogen peroxide sensor operatively coupled to the voltage controller, the hydrogen peroxide sensor being configured to detect a value of the concentration of hydrogen peroxide at the surface; and
wherein the voltage controller is configured to adjust the applied voltage differential between the first and second materials to achieve a setpoint of the concentration of hydrogen peroxide.

2. The dressing of claim 1 wherein the first material and the second material individually include a fabric constructed from an electrically semi-conductive or conductive material.

3. The dressing of claim 1 wherein:
the first material and the second material individually include a fabric constructed from an electrically conductive material; and
the dressing further includes an insulation material between the first and second materials, the insulation material electrically insulating the first material from the second material.

4. The dressing of claim 1 wherein:
the first material and the second material individually include a fabric constructed from an electrically conductive material;
the dressing further includes an insulation material between the first and second materials, the insulation material electrically insulating the first material from the second material; and
the insulation material is permeable to oxygen.

5. The dressing of claim 1 wherein the voltage controller is configured to allow adjustment of the applied voltage differential between the first and second materials.

6. The dressing of claim 1 wherein the voltage controller is configured to:
receive a user input containing the concentration of hydrogen peroxide at the surface; and
adjust the applied voltage differential between the first and second materials to achieve the concentration of hydrogen peroxide in the user input based on a correlation between the voltage differential and the concentration of hydrogen peroxide at the surface.

7. A kit for reducing or preventing bacterial infection to an open wound, the kit comprising:
a dressing having a first material and a second material spaced apart and electrically insulated from the first material, the first and second materials being absorbent to water;
a first electrode and a second electrode electrically couplable to the first and second materials, respectively; and
instruction literature containing instructions for applying an electrical bias to the first and second electrodes at a voltage differential that is calibrated based on a correlation between the voltage differential and a concentration of hydrogen peroxide ($H_2O_2$) produced via an electrochemical reaction between oxygen and water at the surface of the wound as follows: $O_2 + 2H^+ + 2e^- \leftrightarrows H_2O_2$;
a power source electrically couplable to the first and second electrodes, the power source being configured to apply the electrical bias contained in the instructions;
a voltage sensor configured to detect the voltage differential between the first and second materials;
a voltage controller configured to adjust the applied voltage differential between the first and second electrodes to achieve the concentration of hydrogen peroxide based on the detected voltage differential between the first and second materials;
wherein the dressing further includes a hydrogen peroxide sensor operatively coupled to the voltage controller, the hydrogen peroxide sensor being configured to detect a value of the concentration of hydrogen peroxide at the surface; and wherein the voltage controller is configured to adjust the applied voltage differential between the first and second materials to achieve a setpoint of the concentration of hydrogen peroxide.

8. The kit of claim 7 wherein the first material and the second material individually include a fabric constructed from an electrically semi-conductive or conductive material.

9. The kit of claim 7 wherein:
the first material and the second material individually include a fabric constructed from an electrically conductive material; and
the dressing further includes an insulation material between the first and second materials, the insulation material electrically insulating the first material from the second material.

10. The kit of claim 7 wherein:
the first material and the second material individually include a fabric constructed from an electrically conductive material;
the dressing further includes an insulation material between the first and second materials, the insulation material electrically insulating the first material from the second material; and
the insulation material is permeable to oxygen.

11. A dressing for reducing or preventing bacterial infection to an open wound, the dressing comprising:
a first material configured to contact a surface of the open wound;
a second material spaced apart from the first material;
first and second electrodes electrically coupled to the first and second materials, respectively; and
a voltage controller having output electrically coupled to the first electrode at a first polarity and to the second electrode at a second polarity opposite the first polarity, wherein the voltage controller is configured to adjustably bias the first and second materials via the first and second electrodes to a voltage differential corresponding to a concentration of hydrogen peroxide (H2O2) via an electrochemical reaction between oxygen and water at the surface of the wound as follows: $O_2 + 2H^+ + 2e^- \leftrightarrows H_2O_2$;
a voltage sensor operatively coupled to the voltage controller, the voltage sensor being configured to detect the voltage differential between the first and second materials; and the voltage controller is configured to maintain the voltage differential at approximately a setpoint based on the detected voltage differential between the first and second materials, wherein the voltage controller is also configured to:
receive a user input containing a concentration of hydrogen peroxide; and
adjust the applied voltage differential between the first and second materials to achieve the concentration of hydrogen peroxide in the user input based on a correlation between the voltage differential and the concentration of hydrogen peroxide.

12. The dressing of claim 11 wherein the first material and the second material individually include a fabric constructed from an electrically semi-conductive or conductive material.

13. The dressing of claim 11 wherein:
the first material and the second material individually include a fabric constructed from an electrically conductive material; and
the dressing further includes an insulation material between the first and second materials, the insulation material electrically insulating the first material from the second material.

14. The dressing of claim 11 wherein:
the first material and the second material individually include a fabric constructed from an electrically conductive material;
the dressing further includes an insulation material between the first and second materials, the insulation material electrically insulating the first material from the second material; and
the insulation material is permeable to oxygen.

15. The dressing of claim 11 wherein the voltage controller is configured to receive a use input and in response, allow adjustment of the applied voltage differential between the first and second materials.

16. The dressing of claim 11 wherein:
the dressing further includes a hydrogen peroxide sensor operatively coupled to the voltage controller, the hydrogen peroxide sensor being configured to detect a value of the concentration of hydrogen peroxide at the surface; and
the voltage controller is configured to adjust the applied voltage differential between the first and second materials to achieve a setpoint of the concentration of hydrogen peroxide.

* * * * *